(12) United States Patent
Sampath

(10) Patent No.: US 9,308,217 B2
(45) Date of Patent: Apr. 12, 2016

(54) TARGETING GLIOMA STEM CELLS BY SEQUENCE-SPECIFIC FUNCTIONAL INHIBITION OF PRO-SURVIVAL ONCOMIR-138

(75) Inventor: Prabha Sampath, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/996,114

(22) PCT Filed: Dec. 20, 2011

(86) PCT No.: PCT/SG2011/000443
§ 371 (c)(1),
(2), (4) Date: Jun. 20, 2013

(87) PCT Pub. No.: WO2012/087242
PCT Pub. Date: Jun. 28, 2012

(65) Prior Publication Data
US 2013/0281514 A1    Oct. 24, 2013

Related U.S. Application Data

(60) Provisional application No. 61/424,898, filed on Dec. 20, 2010.

(51) Int. Cl.
| | | |
|---|---|---|
| C12N 15/11 | (2006.01) |
| C07H 21/04 | (2006.01) |
| A61K 31/7088 | (2006.01) |
| C12N 15/113 | (2010.01) |
| C12Q 1/68 | (2006.01) |

(52) U.S. Cl.
CPC .......... *A61K 31/7088* (2013.01); *C12N 15/113* (2013.01); *C12Q 1/6886* (2013.01); *C12N 2310/113* (2013.01); *C12N 2310/315* (2013.01); *C12N 2310/531* (2013.01); *C12N 2740/16043* (2013.01); *C12Q 2600/118* (2013.01); *C12Q 2600/158* (2013.01); *C12Q 2600/178* (2013.01)

(58) Field of Classification Search
CPC ........................ C12N 15/113; C12N 2310/141
See application file for complete search history.

(56) References Cited

U.S. PATENT DOCUMENTS

2005/0261218 A1 * 11/2005 Esau et al. ............... 514/44

FOREIGN PATENT DOCUMENTS

| WO | WO 2005/078139 A2 | 8/2005 |
| WO | WO 2006/137941 A2 | 12/2006 |
| WO | WO 2007/112754 A2 | 10/2007 |
| WO | WO 2008/095096 A2 | 8/2008 |

OTHER PUBLICATIONS miRBase Database Submission, Accession No. MI0000455. Stem-loop sequence hsa-mir-138-2. <http://www.mirbase.org/cgi-bin/mirna_entry.pl?acc=MI0000455> [last accessed Nov. 20, 2013].
miRBase Database Submission, Accession No. MI0000476. Stem-loop sequence hsa-mir-138-1. <http://www.mirbase.org/cgi-bin/mirna_entry.pl?acc=MI0000476> [last accessed Nov. 20, 2013].
Chan et al., MicroRNA-21 is an antiapoptotic factor in human glioblastoma cells. Cancer Res. Jul. 15, 2005;65(14):6029-33.
Corsten et al., MicroRNA-21 knockdown disrupts glioma growth in vivo and displays synergistic cytotoxicity with neural precursor cell delivered S-TRAIL in human gliomas. Cancer Res. Oct. 1, 2007;67(19):8994-9000.
Godlewski et al., microRNA-451: A conditional switch controlling glioma cell proliferation and migration. Cell Cycle. Jul. 15, 2010;9(14):2742-8. Epub Jul. 30, 2010.
Guessous et al., microRNA-34a is tumor suppressive in brain tumors and glioma stem cells. Cell Cycle. Mar. 15, 2010;9(6):1031-6. Epub Mar. 15, 2010.
Landgraf et al., A mammalian microRNA expression atlas based on small RNA library sequencing. Cell. Jun. 29, 2007;129(7):1401-14.
Li et al., MicroRNA-34a inhibits glioblastoma growth by targeting multiple oncogenes. Cancer Res. Oct. 1, 2009;69(19):7569-76. doi: 10.1158/0008-5472.CAN-09-0529. Epub Sep. 22, 2009.
Lui et al., Patterns of known and novel small RNAs in human cervical cancer. Cancer Res. Jul. 1, 2007;67(13):6031-43.
Silber et al., miR-124 and miR-137 inhibit proliferation of glioblastoma multiforme cells and induce differentiation of brain tumor stem cells. BMC Med. Jun. 24, 2008;6:14. doi: 10.1186/1741-7015-6-14.
11849941.7, May 20, 2015, Extended European Search Report.
Zhao et al., miR-138 might reverse multidrug resistance of leukemia cells. Leuk Res. Aug. 2010;34(8):1078-82. doi: 10.1016/j.leukres. 2009.10.002. Epub Nov. 6, 2009.

* cited by examiner

*Primary Examiner* — Dana Shin
(74) *Attorney, Agent, or Firm* — Wolf, Greenfield & Sacks, P.C.

(57) ABSTRACT

Methods for malignant glioma diagnosis/prognosis using miR-138 as a prognostic biomarker and methods for treating malignant glioma and inhibiting glioma stem cell growth by suppressing miR-138. Also disclosed herein are pharmaceutical compositions for use in treating malignant glioma, prolonging survival of malignant glioma patients, or eliminating GSCs and in turn tumor growth, the pharmaceutical composition comprising an oligonucleotide that targets miR-138.

3 Claims, 15 Drawing Sheets

A.

B.

C.

D.

E.

A.

B.

C

D.

E.

A.

B.

C

D

E.

F.

G.

A

B

C.

A.

B.

C.

A.

B.

C.

D.

A.

B

A

B

C.

TARGETING GLIOMA STEM CELLS BY SEQUENCE-SPECIFIC FUNCTIONAL INHIBITION OF PRO-SURVIVAL ONCOMIR-138

RELATED APPLICATIONS

This application is a national stage filing under 35 U.S.C. 371 of International Application PCT/SG2011/000443, filed Dec. 20, 2011, which claims priority to U.S. Provisional Application No. 61/424,898, filed on Dec. 20, 2010, the content of each of which is hereby incorporated by reference herein.

BACKGROUND OF THE INVENTION

MicroRNAs (miRNAs) are endogenous small noncoding RNAs that regulate various physiological pathways such as cellular differentiation and proliferation via gene silencing. More specifically, they bind to complementary sequences in target mRNAs and suppress target gene expression.

Alterations in miRNA expression are known to play a critical role in cancer initiation, progression and metastasis (Calin and Croce, 2006; Ma et al., 2007). The robust connection between miRNAs and tumorigenesis is emphasized by the differential expression profiles of miRNAs from healthy tissue across cancers (Ambros, 2004; Bagga and Pasquinelli, 2006; Bartel, 2004). Several miRNAs have been found to be aberrantly expressed in solid tumors as determined by high throughput microarray techniques. In addition, recent evidence indicates that miRNAs might also function as tumor suppressors or activators. Examples include miR-127, and miR-15a/miR-16-1, which target BCL6 and BCL2 anti-apoptotic genes, respectively, and the let-7 family members, which target the Ras oncogenes (Esquela-Kerscher and Slack, 2006; Slack and Weidhaas, 2006). Further, impaired miRNA regulatory network is known to be one of the key mechanisms in brain tumor pathogenesis (Bottoni et al., 2005; Chan et al., 2005).

Malignant gliomas account for approximately 70% of the 22,500 new cases of malignant primary brain tumors that are diagnosed in adults in the United States each year. Malignant gliomas (MG) comprise of grade-III anaplastic astrocytoma and grade-IV glioblastoma multiforme (GBM) lesions that are highly invasive and display histological evidence of malignancy. GBM is a lethal intracranial malignancy with a median survival of less than 12 months (Legler et al., 1999). Composed of a heterogeneous mixture of poorly differentiated neoplastic astrocytes, malignant gliomas primarily affect adults, and preferentially occur in the cerebral hemispheres. Treatment of malignant gliomas is palliative and includes surgery, radiotherapy, and chemotherapy and frequently recur after radiation as focal masses (Garden et al., 1991).

Despite the recent advances in malignant glioma treatment, patients relapse after an initially favorable response to therapies. This is potentially due to a sub-population of cells with tumorigenic potential that are intrinsically resistant to therapy. These cells, referred to as tumor-initiating "stem cells" or cancer stem cells, were identified in a variety of solid tumors including brain tumors (Galli et al., 2004; Hemmati et al., 2003; Singh et al., 2004). This cellular fraction of the tumors is capable of initiating tumors similar to the parental tumor when transplanted into a secondary site (Reya et al., 2001).

It has been found that a malignant glioma is a heterogeneous tumor composed of a small portion of tumor-initiating cells, i.e., glioma stem cells (GSCs). GSCs are phenotypically similar to normal neural stem cells (NSCs). They express CD133 and Nestin, which are characteristic marks for NSCs. Like NSCs, GSCs also possess the self-renewal potential. On the other hand, GSCs have the potential to recapitulate original polyclonal tumors when xeno-grafted to nude mice. They are chemo-resistant and radiation-resistant and therefore responsible for tumor progression and recurrence after conventional therapy.

Altered expression (e.g., reduced/loss-of expression) of a miRNA may lead to aberrant expression of its target proteins, resulting in altered phenotype. For example, overexpression of miR-34a inhibits proliferation, disrupts tumorsphere formation, or induces differentiation of GSCs, but fails to eliminate GSCs (Guessous et al., 2010; Li et al., 2009).

SUMMARY OF THE INVENTION

The present invention is based on unexpected discoveries that (i) the levels of microRNA-138 (miR-138) increase in glioma stem cells (GSCs) isolated from MG patients and in GBM patient tumor samples (primary and secondary) as compared to those in normal neural stem cells (NSCs) and in healthy controls, and (ii) knockdown of miR-138 results in suppression of cell proliferation, induction of apoptosis, and reduction of tumorigenicity. These discoveries demonstrate that miR-138 is a reliable biomarker for monitoring brain tumor progress, assessing efficacy of MG treatment, and identifying GSCs, the presence of which is indicative of an increased risk in MG development, progression, and metastasis. They also demonstrate that miR-138 is a target in treating malignant glioma, such as grade-III anaplastic astrocytoma and grade-IV glioblastoma multiforme.

Accordingly, one aspect of this disclosure relates to a method for treating malignant gliomas, including administering to a subject in need thereof an effective amount of an oligonucleotide (an antigomir) specifically targeting miR-138, which can be a hairpin oligonucleotide. The oligonucleotide can comprise a core sequence having the nucleotide sequence of 5'-CGGCCTGATTCACAACACCAGCT-3' (SEQ ID NO:1), which targets the sequence of human mature miR-138. In one example, the oligonucleotide has the nucleotide sequence of 5'-GAGCTGGTATTGTGAATCAAG-CAGCTTCCTGTCAGCGGCCTGATTC ACAACAC-CAGCTTTTTT-3' (SEQ ID NO:2). In another example, one or more of the nucleotides in the oligonucleotide are modified by, e.g., a 2'-O-methoxyethyl group, a 2'-O-methoxy group, or a phosphorothioate group.

In another aspect, the present disclosure provides a method for inhibiting GSC cell growth, including contacting GSCs with an effective amount of any of the oligonucleotides described above. In this method, the contacting step can be performed by administering the oligonucleotide to a subject in need of the treatment.

In yet another aspect, this disclosure provides a method for prolonging survival in malignant glioma patients (e.g., human patients) with an effective amount of any of the above-described oligonucleotides. Optionally, the patients subjected to this method have undergone or are in the course of conventional therapy, including surgery, radiotherapy, and/or chemotherapy.

Any of the methods described above can be performed, when applicable, on a human subject having, suspected of having, or at risk for malignant glioma. The oligonucleotide administered to such a subject can be in an amount sufficient to suppress GSC proliferation or in an amount sufficient to induce GSC apoptosis in the subject.

Also within the scope of this disclosure are (a) a pharmaceutical composition for use in treating MG, prolonging survival of a MG patient, or inhibiting GSC growth, the pharmaceutical composition containing any one or more of the oligonucleotides described herein and a pharmaceutically acceptable carrier; and (b) the use of the just-described pharmaceutical composition in manufacturing a medicament for any of these purposes.

In addition, the present disclosure provides methods for monitoring MG progress, methods for assessing efficacy of a MG treatment, and methods for identifying GSCs, all relying on the level of miR-138 as a biomarker.

A method for monitoring MG progress includes at least the following steps: obtaining samples containing tumor cells from a patient (e.g., a human patient or a laboratory animal) suffering from MG at multiple time points, quantifying the levels of miR-138 in the samples, and assessing whether MG progresses in the subject. An increase in miR-138 levels over time indicates progress of MG. In this method, the quantifying step can be performed by any conventional method, including, e.g., quantitative real-time PCR or in-situ hybridization.

A method for assessing efficacy of a MG treatment in a patient (e.g., a human patient or a laboratory animal) includes obtaining samples containing tumor cells from the patient before, during, and/or after the treatment, quantifying levels of miR-138 in the samples via a conventional method (e.g., those listed above), and assessing efficacy of the treatment based on the level of miR-138. No change or a decrease in the levels of miR-138 after the treatment or along the course of the treatment indicates that the treatment is effective. In some embodiments, the samples are obtained before and after the treatment and no change or a decrease in the level of miR-138 after the treatment indicates that the treatment is effective. In other embodiments, the samples are obtained at multiple intervals during the treatment and no change or a decrease in the levels of miR-138 along the course of the treatment indicates that the treatment is effective.

A method for identifying GSCs includes quantifying the level of miR-138 in a sample suspected of containing GSCs via a conventional method as those described herein, and determining whether the sample contains glioma stem cells based on the level of miR-138. An elevated miR-138 level in the sample as compared to a predetermined standard (e.g., the level of miR-138 in non-tumor cells such as normal neural stem cells) indicates presence of glioma stem cells in the sample. The sample suspected of containing GSCs can be obtained from a human subject. In some embodiments, this method further comprises a step of assessing whether the human subject is suspected of having or at risk for malignant glioma. Presence of GSCs in the sample indicates that the human subject is suspected of having or at risk for malignant glioma. In other embodiments, the method further comprises assessing the risk of tumor progression or tumor metastasis in a malignant glioma patient. Presence of GSCs in the sample is indicative of an increased risk for malignant glioma progression or metastasis.

The details of one or more embodiments of the invention are set forth in the description below. Other features or advantages of the present invention will be apparent from the following drawings and detailed description of several examples, and also from the appended claims.

BRIEF DESCRIPTION OF THE DRAWINGS

The drawings are first described.

DETAILED DESCRIPTION OF THE INVENTION

Figure 1:
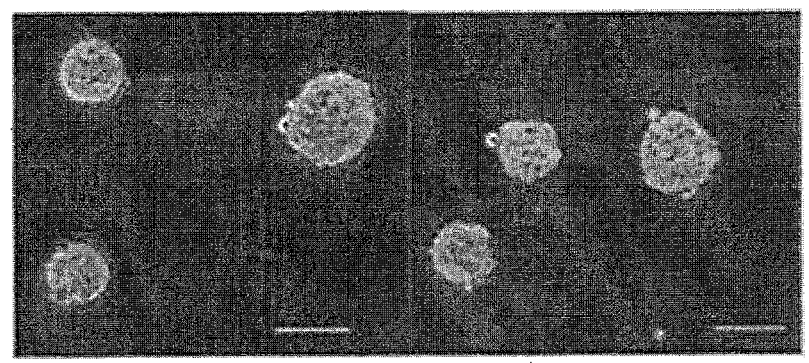
FIG. 1 is a diagram showing that GSCs are multipotent and tumorigenic. A: a photo of representative images showing that, like NSCs, GSCs also form spheres. Scale bar: 100 μm. B: a photo showing immune-blot analysis of cellular lysates from GSCs. NSCs, and GSCs on differentiation. Like NSCs, GSCs express neural stem cell markers CD133 and Nestin. C: a bar graph showing the percentage of tumorspheres formed by GSCs, demonstrating the GSCs' ability to self-renew (left panel) and a photo showing formation of a tumorsphere. Sub-sphere forming assay was performed up to 3 generations. The bar graph represents the mean and standard deviation from triplicate experiments. D: a photo of representative images showing differentiation of GSCs to neurons, astrocytes, and oligodendrocytes, which were determined by specific markers Tuj1, GFAP, and O4, respectively. E: a photo showing characteristic glioblastoma phenotype observed in H&E stained tumor sections via light micrograph.
Figure 1:
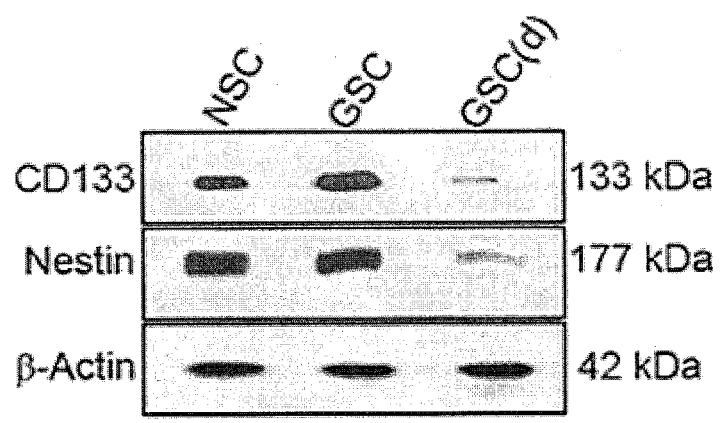
Figure 1:
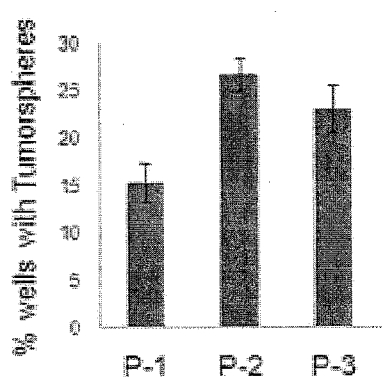
Figure 1:
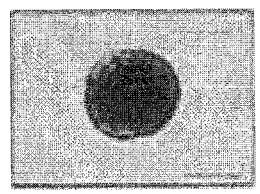
Figure 1:
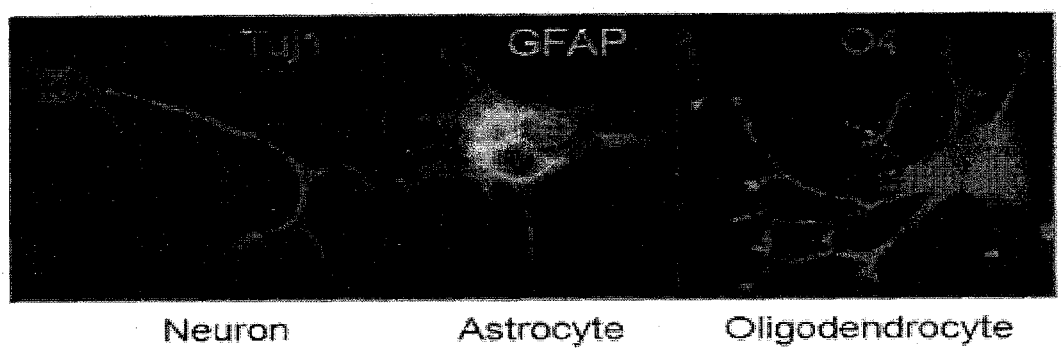
Figure 1:
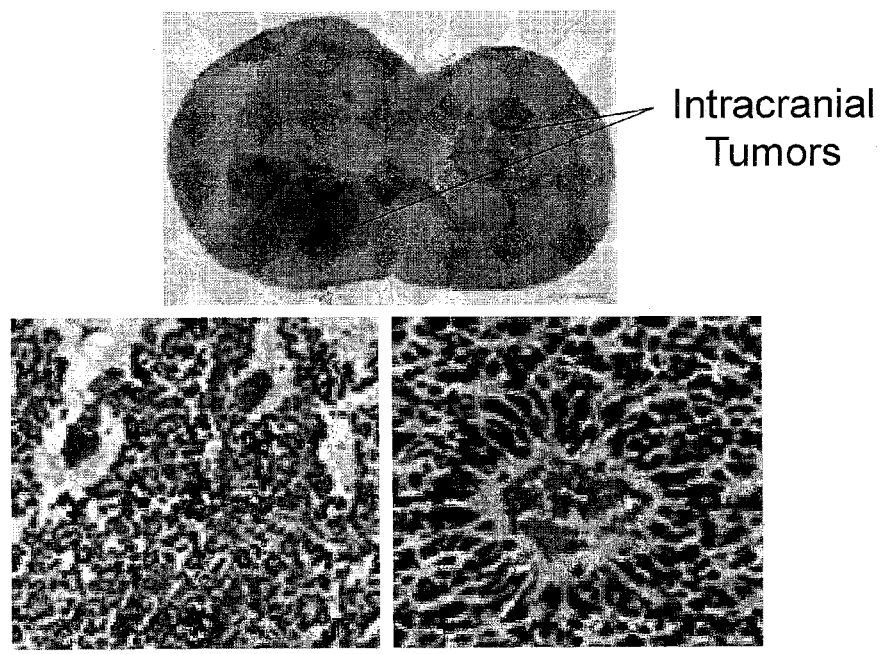

Disclosed herein are methods for treating malignant glioma (MG) by suppressing miR-138 and malignant glioma-related diagnostic and prognostic methods using miR-138 as a biomarker.

miR-138 is a well-characterized endogenous microRNA found in many species, including human and mouse. Information regarding miR-138 can be obtained from the microRNA database (www.mirbase.org) or from GenBank. Two putative precursors, miR-138-1 (GenBank Accession No. MI0000476) and pre-miR-138-2 (GenBank Accession No. MI0000455), have been identified, which are encoded on human chromosomes 3 and 16 and are 99 and 84 nucleotides in length, respectively (Griffiths-Jones, 2004; Lagos-Quintana et al., 2002; Weber, 2005). See also Landgraf et al., Cell 129:1401-1414 (2007) and Lui et al., Cancer Res. 67:6031-6043 (2007). Sequence alignments of the two chromosomal regions show high sequence homology with the mature miRNA. It has been reported that the mature miR-138 is a product of pre-miR-138-2, but not pre-miR-138-1 (Obernosterer et al., 2006). Stringent transcriptional and post-transcriptional control mechanisms regulate the synthesis of mature miR-138 (Obernosterer et al., 2006).

The nucleotide sequences of Pre-miR-138-1, Pre-miR-138-2, and mature miR-138; are provided below:

```
Nucleotide sequence of Pre-miR-138-1 (GenBank Accession No. MI0000476; SEQ ID NO: 62):
  1 ccctggcatg gtgtggtggg gcagctggtg ttgtgaatca ggccgttgcc aatcagagaa 61 cggctacttc acaacaccag ggccacacca cactacagg Nucleotide sequence of Pre-miR-138-2 (GenBank Accession No. MI0000455; SEQ ID NO: 63):
  1 cgttgctgca gctggtgttg tgaatcaggc cgacgagcag cgcatcctct tacccggcta 61 tttcacgaca ccagggttgc atca Nucleotide sequence of mature miR-138 (SEQ ID NO: 64)
  1 .a gctggtgttg tgaatcaggc cg
``` miR-138 as a Target in MG Treatment

In some embodiments, an effective amount of an oligonucleotide that targets miR-138 can be used for treating MG in a subject in need of the treatment. The term "treating" as used herein refers to the application or administration of a composition including one or more active agents to a subject, who has MG, a symptom of the disease, or a predisposition toward the disease, with the purpose to cure, heal, alleviate, relieve, alter, remedy, ameliorate, improve, or affect the disease, the symptoms of the disease, or the predisposition toward the disease.

In other embodiments, an effective amount of the oligonucleotide noted above is used to inhibit glioma stem cell (GSC) growth, either in vitro or in a subject that needs the treatment. Inhibition of GSC growth reduces the risk for malignant glioma development, progression, and/or metastasis.

In yet other embodiments, an effective amount of a miR-138-targeting oligonucleotide is used to prolong survival of malignant glioma patients. Optionally, the malignant glioma patients have undergone, are in the course of, or will be subjected to conventional therapy, such as surgery, radiotherapy, or chemotherapy. A malignant glioma patient subjected to this method is expected to have increased survival prospect as compared to malignant glioma patients with matched factors that may affect survival prospect (e.g., disease severity, age, gender, lifestyle, and conditions unrelated to malignant glioma) and not treated by this method.

"An effective amount" as used herein refers to the amount of an miR-138-targeting oligonucleotide that alone, or together with further doses or one or more other active agents, produces the desired response, e.g., inhibiting GSC growth via suppressing GSC proliferation and/or inducing GSC apoptosis, or prolonging survival of a malignant glioma patient. In the case of treating malignant glioma, the desired response may be inhibiting the progression of tumor growth. This may involve only slowing the progression of MG temporarily, although more preferably, it involves halting the progression of the tumor permanently and/or reducing the volume of the tumor. This can be monitored by routine methods, X-ray analysis, computed tomography (CT), and magnetic resonance imaging (MRI); or can be monitored according to the prognosis/efficacy-assessing methods described herein. The desired response to treatment of MG also can be delaying the onset or even preventing the onset of the tumor, or delaying metastasis or even preventing metastasis of the tumor.

Effective amounts vary, as recognized by those skilled in the art, depending on the particular condition being treated, the severity of the condition, the individual patient parameters including age, physical condition, size, gender and weight; the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The interrelationship of dosages between animals and humans (e.g., based on milligrams per meter squared of body surface or milligrams per body weight) is well known in the art. See, e.g., Freireich et al., (1966) *Cancer Chemother Rep* 50: 219. Body surface area may be approximately determined from height and weight of the patient.

A subject in need of any of the above-described treatments can be a subject (e.g., a human) suffering from MG (e.g., anaplastic astrocytoma or glioblastoma multiforme), suspected of having MG, or at risk for developing MG. A subject having MG can be identified via a routine medical procedures, including, but are not limited to, physical examination, pathological analysis, computed tomography (CT), and magnetic resonance imaging (MRI). A subject suspected of having MG may show one or more symptoms of the disease, including seizure, nausea and vomiting, headache, hemiparesis, and a progressive memory, personality, or neurological deficit due to temporal and frontal lobe involvement. Such subjects can be identified via routine medical procedures. A subject at risk for developing MG possesses one or more risk factors associated with MG. Below is a list of exemplary risk factors for MG:

Sex: male (slightly more common in men that women)
Age: over 50 years old
Ethnicity: Caucasians, Latinos, Asians
Having a low-grade astrocytoma (brain tumor), which occasionally develops into a higher-grade tumor,
Having one of the following genetic disorders: Neurofibromatosis, Tuberous sclerosis, Von Hippel-Lindau disease, Li-Fraumeni syndrome, and Turcot's syndrome, and
Having loss of heterozygosity or a genetic mutation in the p53 gene, the epidermal growth factor receptor gene, the MDM2 gene, the platelet-derived growth factor-alpha gene, the PTEN gene, the MMAC1-E1 gene, the MAGE-E 1 gene, or the NRP/B gene.

An oligonucleotide that targets miR-138 is a nucleic acid molecule (either DNA or RNA), at least a portion of which is complementary (i.e., completely or partially) to a fragment of miR-138, i.e., capable of forming a double-strand duplex with miR-138 via base-pairing according to the standard Watson-Crick complementarity rules. Such an oligonucleotide is capable of reducing the level of endogenous miR-138 or inhibiting miR-138 activity. An miR-138-targeting oligonucleotide, preferably having a maximum length of 100 nucleotides (nts), can be a double-stranded molecule or a hairpin molecule including a 21-23 nt sense sequence (complementary to a fragment of miR-138), a short linker, an antisense sequence, and a polyT tail. It can have a minimum length of 8-11 nt. In one example, at least a portion of the oligonucleotide is complementary to the human mature miR-138 sequence or a fragment thereof. Oligonucleotides targeting miR-138 can be designed in light of the sequence of miR-138, which is well known in the art, by routine technology. See, e.g., Krutzfeldt et al., Nature 438 (7068): 685-689, 2005; and Czech, New England Journal of Medicine 354(11): 2, 2006; Obad et al. Silencing of microRNA families by seed-targeting tiny LNAs. Nat Genet 43, 371-378 (2011).

They can be prepared via conventional methods, e.g., chemical synthesis or in vitro transcription. Their ability to inhibit miR-138 can be verified by routine methods, e.g., those described in the Examples below.

When necessary, the oligonucleotide described above for suppressing miR-138 can include non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability.

In one example, the oligonucleotide to be used in a method as described above has a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166,315; and 5,792,608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3', 5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In another example, the miR-138-targeting oligonucleotide described herein includes one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted $C_1$ to $C_{10}$ alkyl or $C_2$ to $C_{10}$ alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Helv. Chim. Acta, 1995, 78, 486-504.

In yet another example, the oligonucleotide described herein includes one or more modified native nucleobases (i.e., adenine, guanine, thymine, cytosine and uracil). Modified nucleobases include those described in U.S. Pat. No. 3,687,808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of the oligonucleotide to miR-138. These include 5-substituted pyrimidines, 6-azapyrimidines and N-2, N-6 and O-6 substituted purines (e.g., 2-aminopropyl-adenine, 5-propynyluracil and 5-propynylcytosine). See Sanghvi, et al., eds., Antisense Research and Applications, CRC Press, Boca Raton, 1993, pp. 276-278).

To perform any of the methods described above, a miR-138 targeting oligonucleotide can be mixed with a pharmaceutically acceptable carrier to form a pharmaceutical composition. An "acceptable carrier" is a carrier compatible with the active ingredient of the composition (and preferably, stabilizes the active ingredient) and not deleterious to the subject to be treated. Suitable carriers include, but are not limited to, (a) salts formed with cations (e.g., sodium, potassium, ammonium, magnesium, calcium) and polyamines (e.g., spermine and spermidine); (b) acid addition salts formed with inorganic acids (e.g., hydrochloric acid, hydrobromic acid, sulfuric acid, phosphoric acid, nitric acid); (c) salts formed with organic acids (e.g., acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid); and (d) salts formed from elemental anions (e.g., chlorine, bromine, and iodine). Other suitable carriers include microcrystalline cellulose, mannitol, glucose, defatted milk powder, polyvinylpyrrolidone, starch, and a combination thereof. See, e.g., Remington's Pharmaceutical Sciences, Edition 18, Mack Publishing Co., Easton, Pa. (1995); and Goodman and Gilman's "The Pharmacological Basis of Therapeutics", Tenth Edition, Gilman, J. Hardman and L. Limbird, eds., McGraw-Hill Press, 155-173, 2001.

Conventional methods, known to those of ordinary skill in the art of medicine, can be used to administer to a subject in need of the treatment the pharmaceutical composition described above. For example, the pharmaceutical composition described above can be delivered orally or parenterally. Parenteral administration includes intravenous, intraarterial, subcutaneous, intraperitoneal or intramuscular injection or infusion; or intracranial administration (e.g., intrathecal or intraventricular).

An injectable composition containing an oligonucleotide for targeting miR-138 may contain various carriers such as vegetable oils, dimethylactamide, dimethylormamide, ethyl lactate, ethyl carbonate, isopropyl myristate, ethanol, and polyols (glycerol, propylene glycol, liquid polyethylene glycol, and the like). For intravenous injection, the oligonucleotide can be administered by the drip method, whereby a pharmaceutical formulation containing the oligonucleotide and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of a peptide, can be dissolved and administered in a pharmaceutical excipient such as sterile water, 0.9% saline, or 5% glucose solution.

When oral administration is applied, it is preferred that the oligonucleotide includes at least one 2'-O-methoxyethyl modification. A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. The pharmaceutical composition described herein can also be administered in the form of suppositories for rectal administration.

To facilitate delivery, the oligonucleotide can be conjugated with a chaperone agent. As used herein, "conjugated" means two entities are associated, preferably with sufficient affinity that the therapeutic benefit of the association between the two entities is realized. Conjugated includes covalent or noncovalent bonding as well as other forms of association, such as entrapment of one entity on or within the other, or of either or both entities on or within a third entity (e.g., a micelle).

The chaperone agent can be a naturally occurring substance, such as a protein (e.g., human serum albumin, low-density lipoprotein, or globulin), carbohydrate (e.g., a dextran, pullulan, chitin, chitosan, inulin, cyclodextrin or hyaluronic acid), or lipid. It can also be a recombinant or synthetic molecule, such as a synthetic polymer, e.g., a synthetic polyamino acid. Examples of polyamino acids include polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly(2-ethylacryllic acid), N-isopropylacrylamide polymers, and polyphosphazine.

In one example, the chaperone agent is a micelle, liposome, nanoparticle, or microsphere, in which the oligonucleotide/interfering RNA is encapsulated. Methods for preparing such a micelle, liposome, nanoparticle, or microsphere are well known in the art. See, e.g., U.S. Pat. Nos. 5,108,921; 5,354,844; 5,416,016; and 5,527,5285.

In another example, the chaperone agent serves as a substrate for attachment of one or more of a fusogenic or condensing agent.

A fusogenic agent is responsive to the local pH. For instance, upon encountering the pH within an endosome, it can cause a physical change in its immediate environment, e.g., a change in osmotic properties which disrupts or increases the permeability of the endosome membrane, thereby facilitating release of the miR-138-targeting oligonucleotide into host cell's cytoplasm. A preferred fusogenic agent changes charge, e.g., becomes protonated at a pH lower than a physiological range (e.g., at pH 4.5-6.5). Fusogenic agents can be molecules containing an amino group capable of undergoing a change of charge (e.g., protonation) when exposed to a specific pH range. Such fusogenic agents include polymers having polyamino chains (e.g., polyethyleneimine) and membrane disruptive agents (e.g., mellitin). Other examples include polyhistidine, polyimidazole, polypyridine, polypropyleneimine, and a polyacetal substance (e.g., a cationic polyacetal).

A condensing agent interacts with the oligonucleotide, causing it to condense (e.g., reduce the size of the oligonucleotide), thus protecting it against degradation. Preferably, the condensing agent includes a moiety (e.g., a charged moiety) that interacts with the oligonucleotide via, e.g., ionic interactions. Examples of condensing agents include polylysine, spermine, spermidine, polyamine or quaternary salt thereof, pseudopeptide-polyamine, peptidomimetic polyamine, dendrimer polyamine, arginine, amidine, protamine, cationic lipid, cationic porphyrin, and alpha helical peptide.

miR-138 as a Biomarker in MG Diagnosis and Prognosis

As disclosed herein, miR-138 is a reliable biomarker for GSCs, which play crucial roles in MG initiation, progression, and metastasis. Presence of GSCs in a subject is indicative of an increased risk for MG occurrence (including occurrence of grade-III anaplastic astrocytoma or grade-IV glioblastoma multiforme), progression, and/or metastasis.

Accordingly, described herein is a method for identifying GSCs in a sample suspected of containing GSCs. Such a sample (e.g., a brain tumor biopsy sample), can be obtained from a subject having MG or suspected of having the tumor. A conventional method, such as quantitative real-time PCR and hybridization, can be performed to quantify the amount of miR-138 in the sample. Oligonucleotide primers or probes complementary to a portion of miR-138 (either the precursor form or the mature form) can be designed for amplifying miR-138 or hybridizing to this micro RNA. It was within the knowledge of a skilled person to design primers for amplification of miR-138. Oligonucleotide probes specific to miR-138, optionally having a minimum length of 15 nts, are capable of hybridizing to this target miRNA under, e.g., stringent hybridization conditions. As used herein, the term "stringent conditions" refers to parameters known to those skilled in the art. One example of stringent conditions is hybridization at 65° C. in hybridization buffer (3.5×SSC, 0.02% Ficoll, 0.02% polyvinyl pyrolidone, 0.02% bovine serum albumin (BSA), 25 mM $NaH_2PO_4$ (ph 7), 0.5% SDS, 2 mM EDTA). SSC is 0.15M sodium chloride/0.15M sodium citrate, pH7; SDS is sodium dodecylsulphate; and EDTA is ethylene diamine tetra acetic acid. There are other conditions, reagents, and so forth which can be used, which result in the same degree of stringency. A skilled artisan will be familiar with such conditions, and thus they are not given here. The probes for detecting miR-138 can be modified in the same manner as noted above.

The miR-138 amount thus determined, which can be normalized against the cell number if necessary, is compared with a predetermined standard. An elevated level of miR-138 in the sample indicates presence of GSCs. The predetermined standard represents the average amount of miR-138 in non-tumor cells, e.g., normal brain cells, which preferably are from subjects with matched age, sex, and/or ethnic background. In one example, the predetermined standard is the level of miR-138 in neural stem cells.

As also disclosed herein, high levels of miR-138 was observed in recurrent GBM patients as compared with healthy controls. Thus, the level of this microRNA is a prognostic biomarker indicating recurrence of GBM.

To determine whether a patient is suffering from GBM recurrence, a biosample (e.g., a brain tissue biopsy) can be obtained from a patient suspected of having GBM recurrence and the amount of miR-138 can be determined via any method known in the art. The miR-138 level can be compared with a predetermined standard to determine whether the patient has GBM, and if so, the stage of the disease. More specifically, if the miR-138 level in the sample is higher than the predetermined standard, it indicates that the patient has a relapse of GBM and as a malignant tumor, indicates poor survival rates. The predetermined standard represents the average amount of miR-138 in non-glioblastoma patients (e.g., healthy control subjects) or in patients first detected with MG. Preferably, the predetermined standard is obtained from patients with matched age, sex, and/or ethnic background relative to the MG patient whose disease stage needs to be determined.

To monitor MG progression in a patient, biosamples such as those described above can be obtained from the patient at multiple time points and the amounts of miR-138 in the samples are measured via a routine method. If the amount of miR-138 increases over time, it indicates that MG is progressing in the patient.

Given the association between miR-138, MG and increased expression of this microRNA in recurrent GBMs, this can be used as a biomarker to assess efficacy of a MG treatment. To perform this method, biosamples can be obtained from a subject having MG before, during, or after a MG treatment. The amounts of miR-138 in the samples can be determined by a routine method. In one example, a pre-treatment sample and a post-treatment sample are obtained. In another example, samples at multiple time intervals during a treatment can be obtained. If the miR-138 level remains unchanged or decreases after the treatment or along the course of the treatment (that is, the levels of miR-138 remain the same or are lower in samples taken at intervals later in the course of the treatment as compared to those in samples taken at intervals earlier in the course of the treatment), it indicates that the treatment is effective. This method can be applied to a human MG patient to evaluate whether the patient is responsive to a MG treatment. It also can be applied to a laboratory animal used in developing new MG treatment.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference for the purposes or subject matter referenced herein.

EXAMPLES

Methods

Cell Culture and MG Sample Collection

GSC cell lines used in the study were derived from five malignant glioma patient samples NNI-1, NNI-4, NNI-8, NNI-11, and NNI-12. Briefly, the GSC cell lines were cultured in chemically defined serum-free selection growth medium consisting of 20 ng/ml basic fibroblast growth factor (bFGF), 20 ng/ml epidermal growth factor (EGF), 20 ng/ml human recombinant leukemia inhibitory factor (LIF), 5 ug/ml heparin, serum-free supplement (B27) in a 3:1 mix of Dulbecco's modified Eagle's medium (DMEM) and Ham's F-12 Nutrient Mixture (F12). The cultures were incubated at 37° C. in a water-saturated atmosphere containing 5% $CO_2$. Growth factors were replenished every other day. Tumorsphere cultures were expanded by mechanical trituration using a flame-drawn glass Pasteur pipette.

Normal human neural stem cells (NSCs) were obtained from Lonza. NSCs were cultured as free-floating neurospheres in a serum-free DMEM/F12 medium (Invitrogen) supplemented with basic fibroblast growth factor (bFGF, 20 ng/ml, Peprotech), endothelial growth factor (EGF, 10 ng/ml, Peprotech), 2 µg/ml heparin (Sigma) and 2% B27 (Invitrogen).

Lenti-X 293T (Clontech) were cultured according to the supplier's instructions. Human MG specimens for in situ hybridization were obtained from the National University Hospital (NUH).

Cell Differentiation:

Differentiation studies were conducted by allowing GSCs to attach to glass coverslip coated with Laminin and poly-L-ornithine (Sigma). Cells were cultured in differentiation medium containing 12% FBS without growth factors. Fresh medium was replenished every 2 days. Cells were allowed to differentiate for 5-7 days.

Immunocytochemistry on Differentiated GSCs:

Cells plated on coverslips were fixed in PBS containing 4% Para formaldehyde for 30 min at room temperature. Cells were then permeabilized for 5 min in PBS containing 0.2% Tween-20 (omitting O4 staining), rinsed for 5 min in PBS and blocked for 1 hour in PBS containing 10% normal goat serum. Cells were incubated overnight with the following primary antibodies: anti-GFAP (Sigma), anti-β-Tubulin (Covance), anti-O4 (Millipore) and then washed with PBS three times prior to incubation with the appropriate goat secondary antibodies: anti-mouse Alexa 568 (Invitrogen) or anti-rabbit Alexa 488 (Invitrogen) or anti-mouse Alexa 488 IgM (Invitrogen) for 1 hour at room temperature. Cells were then washed with PBS three times. Prior to mounting, nuclei were counterstained with DAPI (5 µg/ml, Invitrogen) and imaging done with a Olympus FV1000 confocal microscope.

Tumorsphere Formation Assay:

Spheres were harvested and dissociated into single cells. Further, single cells were plated into 96-well by manual picking. After plating, cells were observed and only wells with single cell were considered. The number of wells with tumor spheres was scored after 21 days.

MiRNA Profiling:

Total RNAs from GSCs and NSCs was isolated using Exiqon kit following manufacturer's protocol. RNA was subjected to quality control analysis by nano-drop and Bioanalyzer to assess the concentration, integrity of the RNAs and the content of small RNAs. Further, the RNAs thus obtained was subjected to miRCURY™ LNA Array microRNA profiling (Exiqon) following manufacturer's protocol. Arrays were scanned in ozone free environment. Image analysis was performed to quantify the signals on the arrays. Technical quality assessment was performed based on results from spike in controls, flagging of spots, background intensity levels and signal intensity distribution. After background subtraction and normalization, differential gene expression analysis was performed on, e.g., log 2(Hy3/Hy5) ratios including the top-50 miRNA (lowest p-value). A multiple ANOVA model was used to remove batch effects from replicate samples.

Microarray Analysis of Gene Expression Profile:

Total RNA (500 ng) from three biological replicates of GSCs transduced with antimiR-138 or scrambled control samples were converted to biotinylated cRNA using TargetAmp Nano-g Biotin-aRNA labeling kit (Epicentre, Madison, Wis.). Biotinylated RNA was isolated using Qiagen mini columns according to the manufacturer's instructions. cRNA was hybridized on HumanWG-6 v3.0 array chips from Illumina (Illumina Inc., San Diego, Calif.), washing and scanning steps were performed according to the Illumina BeadStation 500× manual. The data was extracted, normalized, and analyzed using Illumina BeadStudio provided by the manufacturer. Transcript signals that were below the limit of detection (LOD) at 99% confidence were defined as genes not expressed. Microarray analysis was performed on PARTEK platform. Gene datasets specific for each group of cells were uploaded onto Ingenuity Pathway Analysis platform (Ingenuity Systems, Mountain View, Calif.) for analysis of biological process, molecular functions and pathways.

RNA Isolation and Quantitative RT-PCR:

Total RNA was extracted using miRCURY RNA isolation kit according to the manufacturer's instructions (Exiqon, Denmark). Reverse transcription (RT) reaction for cDNA synthesis was performed using superscript III (Invitrogen) according to the manufacturer's instructions. Transcript levels were measured by quantitative RT-PCR using SYBR Green PCR master mix (Applied Biosystems). Gene specific primers, shown in Table 1 below, used in this study are listed in supplementary table 1. For miRNA expression analysis, 10 ng total RNA was used along with miR138-specific primers (Taqman MicroRNA assay). cDNA was synthesized using TaqMan miRNA reverse transcription kit and expression level of miRNA levels were analyzed using the 7900 fast Real-time PCR system (Applied biosystems). All reactions were run in triplicate. A U6 TaqMan probe was used as an endogenous control. The comparative Ct (ΔΔCt) method was used to determine the transcript abundance.

TABLE 1

Primers Used in RT-PCR Analysis

| GENE ID | Forward primer 5'----3' | Reverse primer 5'----3' |
| --- | --- | --- |
| COL4A1 | GCCTCCTGGCTTGCCTGG (SEQ ID NO: 10) | TGGTGGGCCTGGAGTCCCTG (SEQ ID NO: 11) |
| BTG2 | CAGAGCACTACAAACACCACTG (SEQ ID NO: 12) | CTGAGTCCGATCTGGCTG (SEQ ID NO: 13) |
| TUSC2 | GCGGCTGGGGCAGGTTATGG (SEQ ID NO: 14) | CCGAGCTTTGGACCCGCTGG (SEQ ID NO: 15) |
| BLCAP | GTCGGTGGCGAGCTGAGG (SEQ ID NO: 16) | CACCAAGGCAGCAGGGATC (SEQ ID NO: 17) |

TABLE 1-continued

Primers Used in RT-PCR Analysis

| GENE ID | Forward primer 5'----3' | Reverse primer 5'----3' |
|---|---|---|
| EFNA1 | CCCCAGTCCAAGGACCAAG (SEQ ID NO: 18) | CTGTGAGTGATTTTGCCACTG (SEQ ID NO: 19) |
| CCND1 | CCTGGATGCTGGAGGTCTG (SEQ ID NO: 20) | ACATGCAAGTGGCCCCCAG (SEQ ID NO: 21) |
| CDC20 | GGGCTGTCAAGGCCGTAGC (SEQ ID NO: 22) | CCACGGCACTCAGACAGG (SEQ ID NO: 23) |
| CCNA2 | TGATCCCGCCGTCCACTC (SEQ ID NO: 24) | GTGCAACCCGTCTCGTCTTC (SEQ ID NO: 25) |
| CASC4 | CCAACTGGACAACCTCTCC (SEQ ID NO: 26) | GCTGCGGATCAACAGGGGATTC (SEQ ID NO: 27) |
| AURKA | CGGAGTGGCGGAGCGTCAAG (SEQ ID NO: 28) | TGGGCAATGGAGTGAGACC (SEQ ID NO: 29) |
| LASP1 | TCACCACATCCCGACCAG (SEQ ID NO: 30) | CGGCGCTGTAGTCATACACC (SEQ ID NO: 31) |
| CEP55 | CAGATCGCGTCCGCGGGATTC (SEQ ID NO: 32) | TGGTCGCCAAGTCCAAAG (SEQ ID NO: 33) |
| OLIG1 | AGGGCGTTCCTGAAGGGCGTC (SEQ ID NO: 34) | GCGCCTGGGAAACCGCATAG (SEQ ID NO: 35) |
| SERPINA3 | GTGGACCTCGGATTAGCCTC (SEQ ID NO: 36) | GCTCATCGCTGGAACTGATTG (SEQ ID NO: 37) |
| GAPDH | ATTTGGCTACAGCAACAGGG (SEQ ID NO: 38) | TGTGAGGAGGGGAGATTCAG (SEQ ID NO: 39) |
| BCL2 | GGGGAGGATTGTGGCCTTC (SEQ ID NO: 40) | CAGGGCGATGTTGTCCACC (SEQ ID NO: 41) |
| PANX2 | GGTAACAGTTGTCGATCTCCTG (SEQ ID NO: 42) | CCAAGAACTTCGCAGAGGAAC (SEQ ID NO: 43) |
| CASP3 | AGAGGGGATCGTTGTAGAAGTC (SEQ ID NO: 44) | ACAGTCCAGTTCTGTACCACG (SEQ ID NO: 45) |
| TXNIP | AGTGCAAACAGACTTCGGAG (SEQ ID NO: 46) | TTTGTCTCTTGAGTTGGCTGG (SEQ ID NO: 47) |
| MXD1 | AGCCGTTCACCAAATCGACC (SEQ ID NO: 48) | CTCGTCAGAGTCGCTCAC (SEQ ID NO: 49) |
| GADD45A | CCCTGATCCAGGCGTTTTG (SEQ ID NO: 50) | GATCCATGTAGCGACTTTCC (SEQ ID NO: 51) |
| cMYC | CCTCCACTCGGAAGGACTATC (SEQ ID NO: 52) | AAGCTCCGTTTTAGCTCGTTC (SEQ ID NO: 53) |
| HIF1A | CAGCAGCCAGACGATCATGCA (SEQ ID NO: 54) | TGGTCAGCTGTGGTAATCCACTTTCA (SEQ ID NO: 55) |
| U6 | CTCGCTTCGGCAGCACA (SEQ ID NO: 56) | AACGCTTCACGAATTTGCGT (SEQ ID NO: 57) |
| hsa-miR-138-1 | CCCTGGCATGGTGTGGTG (SEQ ID NO: 58) | AGTGTGGTGTGGCCCTGGTG (SEQ ID NO: 59) |
| hsa-miR-138-2 | GTTGCTGCAGCTGGTGTTGTG (SEQ ID NO: 60) | GCCGGGTAAGAGGATGCGCTG (SEQ ID NO: 61) |

MicroRNA Northern Blot Analysis:

Northern blot analysis was carried out using 15 μg of small RNA-enriched total RNA. Briefly, RNAs were separated on 15% denaturing Urea-PAGE, transferred to positively charged nylon membrane (Ambion, Austin, Tex.), and cross linked at 120 mJ in UV Stratagene cross linker 2400. MiR-CURY LNA probes for miR-138 and U6, (Exiqon, Denmark) were end-labeled with T4 polynucleotide kinase followed by hybridization.

Lentiviral Constructs

Stable expression of antimiRs were carried out using miRZip™ expression vector, a third generation HIV-based expression Lentiviral vector provided by System Biosciences, LLC. This vector has a CMV-driven [GFP-T2A-Puromycin] reporter cassette and a H1 promoter upstream of either antigomiR-138 or a control non-targeting small RNA. The hairpin consists of 23 nt sense sequence, a 11 nt short spacer (CTTCCTGTCAG; SEQ ID NO:3), an antisense sequence, 6 Ts (a transcription stop signal for RNA polymerase III). The antigomiR sequence used to construct lentivirus against human mature-miR-138 (pmiRZIP-138) was 5'-GAGCTGGTATTGTGAATCAAGCAGCTTC-CTGTCAGCGGCCTGATTCA CAACAC-CAGCTTTTTT3' (SEQ ID NO:2). The mature functional antigomiR-138 sequence is CGGCCTGATTCACAACAC-CAGCT (SEQ ID NO:1), which is complementary to the mature miR-138 sequence. The H1 expression cassette of the vector provides constitutive and efficient RNA polymerase III-dependent transcription of antigomiR transcripts. CMV promoter promotes high level of expression of both copGFP (fluorescent reporter) and puromycin-Nacetyl transferase (drug selectable marker) in the same vector for detection and selection of transduced cells.

Alternatively, synthetic single-stranded anti-miRNA or antigomiRs were introduced into cells to knock down miR-NAs (i.e., decreasing miRNA levels) transiently.

Preparation of Lentiviral Stocks and Transductions

Third generation lentiviruses were produced in Lenti-X 293T (cat#632180, Clontech, Mountain View, Calif.) devoid of Tat in the packaging mix. A lentiviral packaging mix containing three plasmid constructs, pMDLg/pRRE (cat #12251), pRSV-Rev (cat #12253) and pMD2.G (cat #12259) [Addgene], was used. Super coiled DNA of constructs were prepared by using Qiagen maxi prep kits (cat #1045091, Germantown, Md.). The packaging constructs were used to transfect Lenti-X 293T cells as described in the protocol in Tiscomia et al., 2006. Transducing Units (TU) determination and transductions were performed following the methods also described in Tiscomia et al., 2006. Transfections were performed in antibiotic free medium using EFFECTENE transfection reagent (cat #301427, Qiagen, Germantown, Md.) reagent as per manufacturer protocol. Supernatant was collected 2nd and 3rd day post transfection. Supernatant is pooled and filtered through a 0.45 μm HV Durapore membrane (Millipore #SCHVU01RE) Filtrate is subjected to centrifugation at 25,000 rpm (~82,000 g) for 2h at 4° C. The visible pellet was re-suspended in cold 1×HBSS (cat #9269, Sigma-Aldrich, St. Louis, Mo., USA) and stored at −80° C. or used for transduction.

Titration of Lentivirus

Transducing Units (TU) were determined as per the protocol described also in Tiscornia et al., 2006. Lenti viral titrations were performed in HEK 293T cells. Briefly, HEK293T cells were plated at density of $4\times10^4$/well in 24-well plate. Next day, cells were transduced with serially diluted lentiviruses in the presence of polybrene 8 ug/ml. Three days of post transduction, percentage GFP positive cells were measured using FACS analysis and number of transducing particles was determined. Biological viral titer was determined according to the following formula: TU/ml=(P×N)/(D×V), where TU=Transduction units, P=% GFP positive cells (percentage is between 2-20%), N=Number of cells at the time of transduction, D=Dilution factor, V=Volume of viral inoculum. Further titrations were confirmed by FACS and genomic PCR for integrated Lentiviral genome copies in target cell lines using specific primers as described earlier (Geraerts et al., 2006). Specific primers for WPRE: 5'-CAGGCAACGTG-GCGTGGTG-3' (SEQ ID NO:4) and 5'-GGCGATGAGTTC-CGCCGTG-3' (SEQ ID NO:5); LTR-GAG: 5'-TGTGTGC-CCGTCTGTTGTGTGAC-3' (SEQ ID NO:6), 5'-TCGGGCGCCACTGCTAGA G-3' (SEQ ID NO:7); and for GFP: 5'-AGAGCACCAAAGGCGCCCTG-3' (SEQ ID NO:8); and 5'-TGCGGGTGTTGGTGTAGC-3' (SEQ ID NO:9), were used to determine lentiviral genomic integration.

Soft Agar Assay:

For soft agar assay, single cell suspension was made by ACCUTASE (Invitrogen) treatment and resuspended in complete medium containing 0.3% noble agar (Difco). A total of $2\times10^3$ cells were seeded in each well of 6 well plates (Nunc) containing 1% noble agar. Cells were cultured for 2-3 weeks by supplementing fresh medium with growth factors and, once in every three days. Lentiviral transduced cells were grown in the presence of 1 ug/ml puromycin. At the end of the experiment, cells were incubated with 1 mg/ml 3-(4,5-dimethylthiazol-2-yl)-2,5-diphenyltetrazolium bromide (MTT, Sigma Aldrich) for 1 hour. Colonies were counted using MATLAB software program.

Cell Viability Assay

Cells infected with lentivirus for 48 h were plated at a density of 5,000 cells/well in 96-well plates in at least triplicate for growth curve analysis. Live cells were determined at the indicated number of days after plating using the Cell Titer-Glo Luminescent Cell Viability Assay kit (Promega).

Luciferase Assay:

Luciferase reporter constructs containing the 3'UTR of BLCAP, CASP3 and MXD1 were purchased from Genecoepia (Rockville, Md.). Total of 50 ng of wild-type or mutated reporter plasmids were cotransfected with 250 ng of pCDH-miR-138 or a negative control vector into HEK293T cells using EFFECTENE following the manufacturer's protocol (Qiagen). Firefly and Renilla luciferase activities were measured at 48 hours of post-transfection using Dual-Luciferase Reporter System (Promega) according to the manufacturer's instructions. The firefly luminescence was normalized to the Renilla luminescence as an internal control for determining transfection efficiency. The experiments were performed in triplicates. miR-138 binding site was mutated using the QuikChange II XL Site-Directed Mutagenesis Kit (Stratagene), in accordance with the manufacturer's instructions. For the mutated constructs, the miR-138 binding site accagc was substituted with cttgat, gaagta and gcagaa in BLCAP, MXD1, and CASP3 respectively.

Caspase 3/7 Assay

GSCs were infected with lentivirus for 2 days. Cells were plated at a density of 5000 cells/well in 96-well lates in at least triplicate. Caspase 3/7 activity was measured by commercially available Caspase-Glo 3/7 assay kit (Promega). Relative luciferase units were calculated based on the number of viable cells, using the CellTiter-Glo Luminescent Cell Viability assay as described above.

Cell-Cycle Analysis and Annexin V Staining

GSCs plated in six-well plates at 100,000 cells per well were infected with Lentiviruses for 48 hours. To determine the percentage of cells in each phase of the cell cycle, cells were labeled with 20 μM EdU for 5 hours prior to harvesting, and processed using the Click-iT EdU Alexa Fluor 647 Flow Cytometry assay kit (Invitrogen), and cell nuclei were counter stained with 25 μg/ml propidium iodide (Sigma-Aldrich). Samples were subject to EdU incorporation analysis on a BD FACS caliber (Becton Dickinson). Data were analyzed using the WIN-MDI 2.9 software. To detect apoptotic cells, Annexin V-FITC staining was performed with the Annexin V-FITC Apoptosis Detection Kit (BD Pharmingen) following manufacturer's protocol.

TUNEL (Terminal Deoxynucleotidyl Transferase (TdT) Nick End Labeling) Assay

Lentiviral transduced spheres were grown for indicated time points and collected by spinning at 900×g. Spheres were washed twice with PBS and paraffin embedded sections were made and attached on 0.01% polylysine-coated slides, fixed with 4% methanol-free formaldehyde solution, bleached with 6% $H_2O_2$ and fluorescence stained by following the procedure of the DeadEnd fluorometric TUNEL system (Promega). Cell nuclei were counter stained with DAPI.

Western Blotting

Equal amount of cell lysate were resolved by SDS-PAGE, transferred to PolyVinylidene difluoride membranes (Millipore), and detected using SuperSignal West Pico (Pierce Biotechnology). All blots were stripped and reprobed with β-actin antibodies (Abcam) as loading control. For immunoblots, primary antibodies used were: anti-PARP (Abcam), anti-LASP1 (Abcam), anti-BTG2 (Abcam), anti-OLIG1 (Abcam), anti-GADD45☐ (Santa Cruz), anti-EFNA1 (Santa Cruz), anti-CYCLIN D1 (Santa Cruz), anti-CDKN1A (Santa Cruz), anti-AURKA (Cell signaling), anti-phospho-Histone3 (Millipore), anti-Pannexin 2 (Santa Cruz), anti-TXNIP (Santa Cruz), Secondary antibodies used were anti-rabbit HRP (Santa Cruz) and anti-mouse HRP (Jackson Laboratory).

Luciferase Assay

Luciferase reporter constructs containing the 3'UTR of BLCAP, CASP3 and MXD1 were purchased from Genecoepia (Rockville, Md.). Total of 50 ng of wild-type or mutated reporter plasmids were cotransfected with 250 ng of pCDH-miR-138 or negative control vector into HEK293T cells using Effectene as per manufactures protocol (Qiagen). Firefly and *Renilla* luciferase activities were measured at 48 hours of post-transfection using Dual-Luciferase Reporter System (Promega) according to the manufacturer's instructions. The firefly luminescence was normalized to the *Renilla* luminescence as an internal control for transfection efficiency. The experiments were performed in triplicates. miR-138 binding site was mutated using the QuikChange II XL Site-Directed Mutagenesis Kit (Stratagene), in accordance with the manufacturer's instructions. For the mutated constructs, the miR-138 binding site accagc was substituted with cttgat, gaagta and gcagaa in BLCAP, MXD1 and CASP3 respectively.

Immunohistochemistry (IHC)

Staining was performed on paraffin tumor sections as previously described (Xue et al, 2010). Briefly, tumor sections from mouse xenograft were dewaxed and rehydrated through descending ethanol concentrations. Tumor sections were stained with anti-GFP (Abcam,) and anti-GFAP (Sigma) after epitope retrieval at pH 6. After 1 hour primary antibody incubation, sections were washed in tap water and incubated for 30 min with HRP-labeled polymer conjugated to goat anti-rabbit IgG (Dako EnVision+Peroxidase system before color development using the 3,3'-diaminobenzidine substrate-chromogen system (Dako). The sections were counter-stained with haematoxylin before dehydrating and mounting in DPX. Photographs were taken using a Nikon eclipse 90i microscope.

miR-138 In Situ Hybridization

For the detection of miR-138, 5' and 3' double DIG labeled LNA probe against miR-138/scramble control probes were used (Exiqon, Denmark). Five micron sections of mouse tumor tissues/GBM tissues were deparaffinized in Xylene and rehydrated. The sections were treated with protease, (Panomics, USA) followed by PBS wash. Slides were fixed and dehydrated. Double DIG labeled miR-138/Scramble LNA probe was hybridized to the sections in microRNA ISH buffer (Exiqon). After hybridization, sections were treated with blocking reagent (Roche) followed by incubation with Goat serum (DAKO). The DIG labeled LNA probes were detected using Alkaline phosphatase conjugated anti-DIG antibody and BM Purple substrate (Roche) at 30° C. Color development was continued until the scramble control LNA probe treated sections show non-specific staining. Slides were dehydrated, passed through Xylene bath and mounted with DPX-neutral mounting medium (Sigma). Images were acquired using Bright field microscope.

Intracranial Implantation of GSCs

Intracranial transplantation of GSCs into 8 weeks old NOD/SCID/IL2rγ mice obtained from Jackson Laboratory, was performed as described in accordance with the Institutional Animal Care and Use Committee approved protocol. Luciferase-expressing GSCs bearing either antimiR-138 or scramble control, were orthotopically transplanted following washing and resuspension in PBS. Three microliters ($15 \times 10^4$ cells) were injected stereotactically into the forebrain of immunodeficient mice. Mice were maintained till the development of neurological symptoms. Brain collected from the euthanized mice, was fixed in 4% paraformaldehyde, paraffin embedded and sectioned. H&E staining was performed according to standard protocol.

GSCs Luciferase Preparation and Bioluminescence Imaging

GSCs Luciferase stables were established by selecting for puromycin (1 μg/ml) after transducing with Lentivirus expressing Luciferase under human PGK promoter (Addgene #w543-1) (Campeau et al. 2009). For bioluminescence imaging, GSCs expressing firefly luciferase bearing scramble-control or antimiR-138 were intracranially injected into the right forebrains of NOD-SCID mice, and the Xenogen system was used for imaging. Mice were given an intraperitoneal dose of 150 mg/kg of D-luciferin and anesthetized in a closed box filled with oxygen and 2-3% isoflurane. Further, animals were imaged after 15 minutes of D-luciferin dosage using the IVIS spectrum Imaging System (Xenogen). Quantification was based on total flux (photons/sec) of emitted light as a measure of the relative number of viable cells. Bioluminescence signals were analyzed using Living Image software (IVIS living image v3.0).

Statistical Analysis

Values are reported as the mean±the standard error. Statistical significance between 2 samples was determined with two-tailed Student's t test using GraphPad InStat 3.0 software (GraphPad Software, Inc.).

Results

GSCs are Multipotent and Tumorigenic

GSCs were derived from tumor specimens obtained from five malignant glioma patients NNI-1, NNI-4, NNI-8, NNI-11 and NNI-12 (see Chong et al., 2009 and Foong et al., 2011) were found to retain their properties for limited passages. A comprehensive validation to test self-renewal properties in vitro and tumorigenic properties in an immune-compromised host was performed on these cell lines. GSCs were first characterized on the basis of functional criteria in comparison with normal human neural stem cell (NSCs). The NSCs used in this study were obtained from Lonza (whole brain-derived), or from specific regions of the human foetal brain (either the frontal cortex or the sub-ventricular zone). In an undifferentiated state, in culture, GSCs form tumorspheres that resemble NSCs derived neurospheres (FIG. 1A). GSCs, like NSCs, express CD133 (Prominin-1) and Nestin. These markers were found to be down-regulated on differentiation (FIG. 1B). To examine the self-renewal capacity of GSCs we performed single cell (clonal) sphere-formation assays (Reynolds, et. al., 2005). When individual spheres from primary culture after enzymatic dissociation were plated as a single cells per well in a 96 well plate and the number of wells with a single cell were scored, 15% of wells formed tumorspheres. When secondary tumorsphere was subjected to sphere formation assay, 26±3% (n=3 independent culture preparations) of wells formed tertiary tumorspheres and quaternary single cell passages yielded 23±5% tumorspheres (FIG. 1C).

Figure 2:
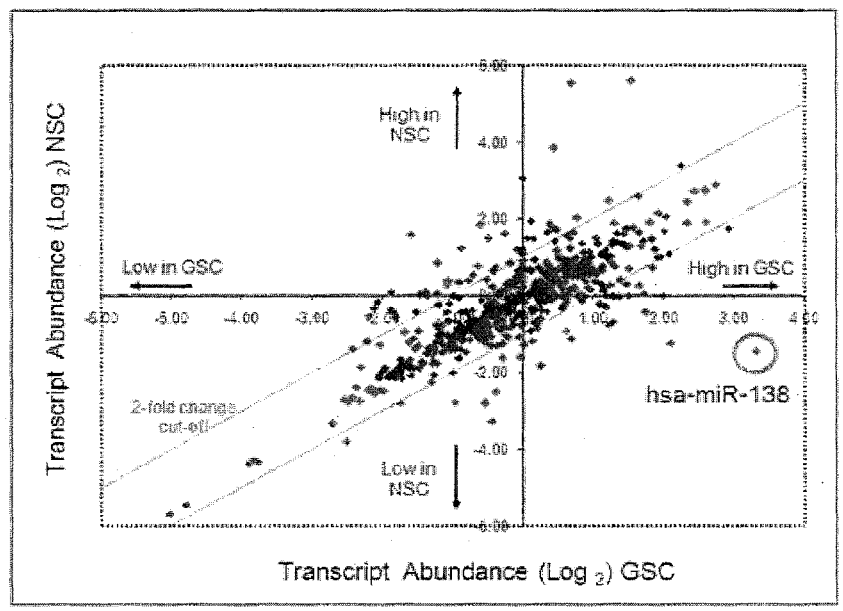
FIG. 2 is a diagram showing identification and validation of differentially expressed miRNAs in GSCs. A: a graph showing differential miRNA expression in GSCs. The scatter plot represents the transcript abundance of miRNAs in GSCs (vertical axis) and NSCs (horizontal axis). B: a bar graph showing levels of miR-138 in NSCs and GSCs as determined by quantitative real-time. PCR (qRT-PCR). C: a photo showing the expression levels of miR-138 in NSCs and GSCs as validated by Northern blot analysis. Blots were re-probed for U6 snRNA as a loading control. D and E: bar graphs showing the expression levels of pre-miR-138-1 and pre-miR-138-2 in NSCs and GSCs and the level of mature miR-138 in GSCs on differentiation, all determined by qRT-PCR.
Figure 2:
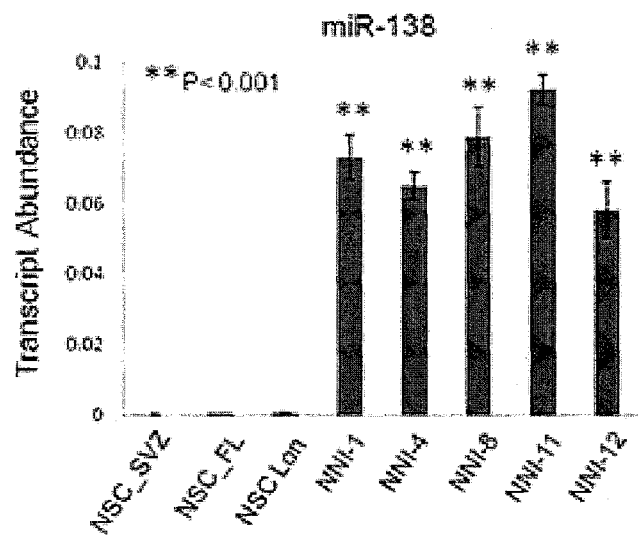
Figure 2:
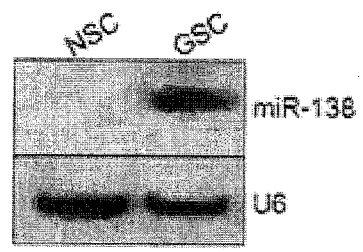
Figure 2:
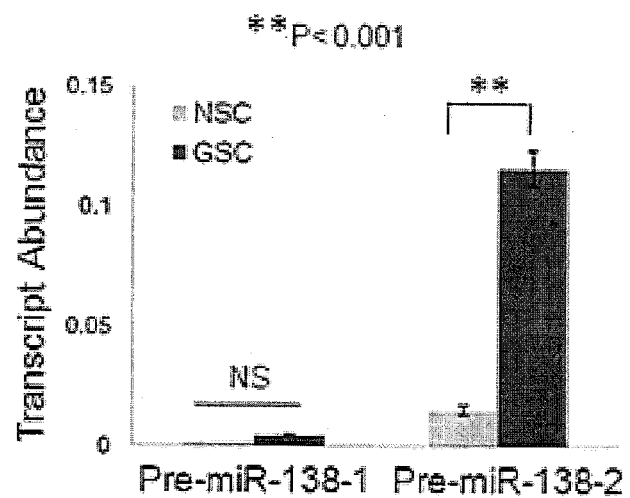
Figure 2:
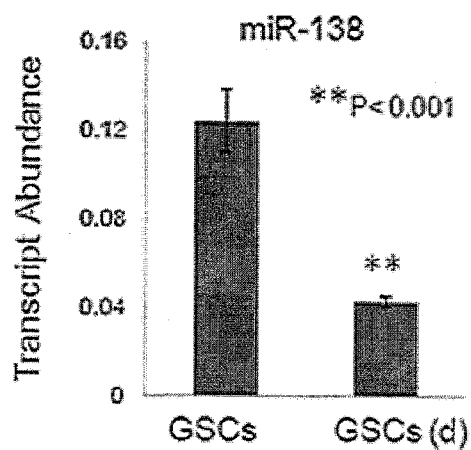

In addition to the self-renewal potential, GSCs, like NSCs, were found to be multipotent and differentiated into neurons, astrocytes and oligodendrocytes (FIG. 1D). However, unlike NSCs, the GSCs were found to be tumorigenic and the first appearance of well-defined tumor masses were observed at 12 weeks after sub-cutaneous injection of GSCs in NOD-SCID mice. Further, GSC-derived xenograft tumor sections were subjected to H&E staining. This histo-pathological analysis of GSC-derived tumors demonstrated a characteristic glioblastoma tissue pattern, e.g., the presence of large areas of necrosis surrounded by highly packed tumor cells. FIG. 1E (see also Bao et al., 2006b; Galli et al., 2004). Some areas show extreme cytologic pleomorphism. Pseudorosettes with tumor cells oriented around a vessel in the center found in human GBMS were also observed. All of these results confirm that GSCs are tumorigenic Identification of Unique miRNA Signatures in GSCs In an attempt to address the tumorigenic property of GSCs, the miRNA expression profiles of GSCs were compared with those of NSCs, using miRNA profiling analysis as described in the Method section above. Differentially expressed miRNAs were identified using ANOVA analysis on normalized microarray data. The scatter plot of the expression data reveals that most of the transcripts were within the 2-fold cut off band, suggesting that the overall miRNA expression pattern in NSCs is very similar to that of GSCs. Among the few differentially expressed transcripts, miR-138 emerged as the most consistent, differentially expressed miRNA. FIG. 2A. GSCs expressed elevated levels of miR-138 compared to the very low or no expression in NSCs. These results was validated by stem-loop real-time reverse transcription-PCR (FIG. 2B) and further confirmed by northern blot analysis using probes that recognize miR-138 (FIG. 2C). It has been demonstrated miR-138 was reliably up-regulated in GSCs relative to their expression in NSCs.

miR-138 has two putative precursors pre-miR-138-1 and pre-miR-138-2, and the synthesis of mature miR-138 is regulated by stringent transcriptional and post-transcriptional control mechanisms. The expression levels of precursor transcripts in GSCs and NSCs were examined. Elevated levels of pre-miR-138-2 were detected only in GSCs, not in NSCs (FIG. 2D), suggesting that miR-138 is under tight transcriptional control in NSCs. The expression levels of miR-138 were then analyzed when GSCs were subjected to differentiation. The result's thus obtained show clear down-regulation of miR-138 in differentiated GSCs. FIG. 2E.

In sum, the results discussed above show that miR-138 is differentially expressed in GSCs and is therefore a reliable biomarker for identifying GSCs, the presence of which is indicative of an increased risk for MG initiation, progression, and metastasis.

Figure 3:
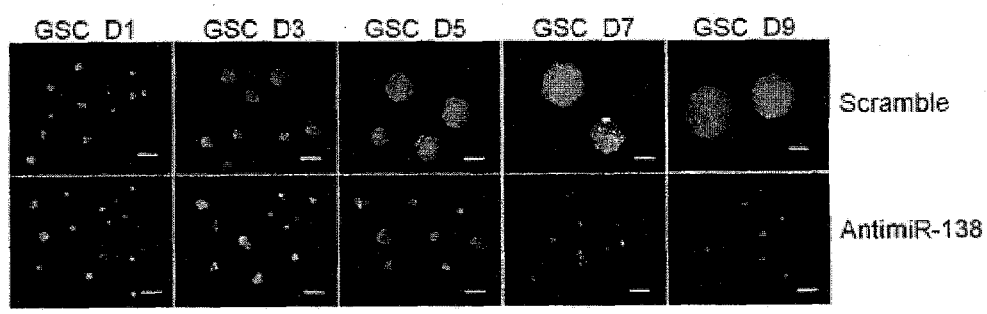
FIG. 3 is a diagram showing functional characterization of differentially expressed miRNAs. A: a photo of representative images showing spheres formed by GSCs transduced with a scramble control (top panel) and antimiR-138 (bottom panel) at various time points. B: a bar graph showing average diameters of tumorspheres at indicated time points formed by GSCs transduced with antimiR-138 or the scramble control. The error bars refer to relative mean±SD of 30 spheres. C: a chart showing the numbers of viable cells in GSCs transduced with the scramble control or antimiR-138 at various time points. D: Inhibition of miR-138 hampered GSC tumorsphere formation. Top panel: a bar graph showing percentage of tumorspheres formed by GSCs transduced by either the scramble control or antimiR-138. Bottom panel: a photo of representative images showing a single-cell-derived tumorsphere formed by GSCs transduced by the scramble control (left) or GSCs transduced by antimiR-138 (right). E: a photo showing colony formation by a soft agar assay using GSCs transduced with scramble control and antimiR-138. F: a photo of representative images showing sphere formation of NSCs transduced with the scramble control (top panel) and antimiR-138 (bottom panel) at various time points. G: a chart showing the expression levels of miR-886, miR-21, miR-1274a and miR-106a in GSCs transduced with the scramble control or antimiR-138.
Figure 3:
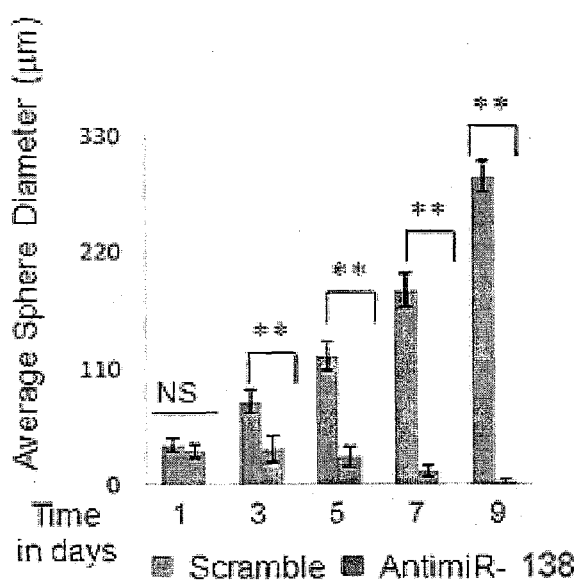
Figure 3:
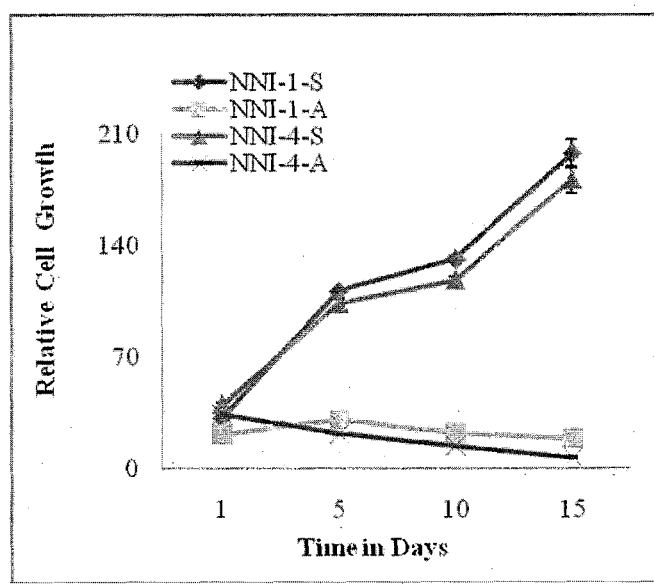
Figure 3:
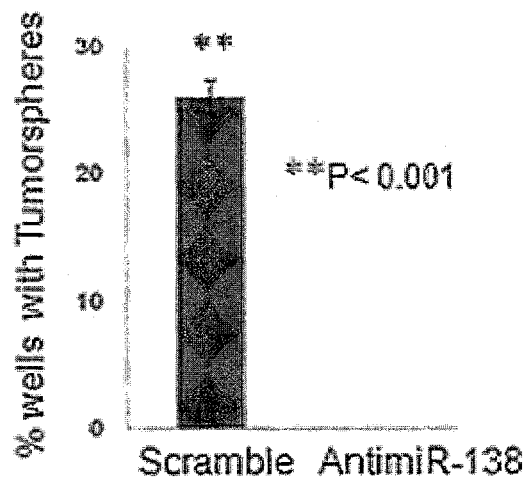
Figure 3:
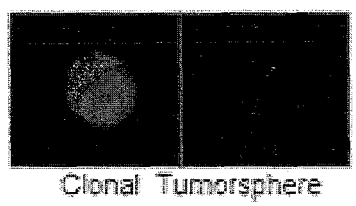
Figure 3:
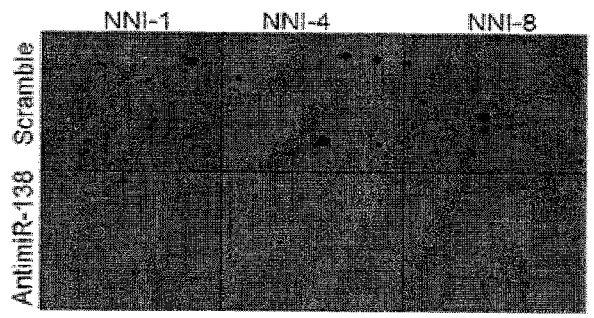
Figure 3:
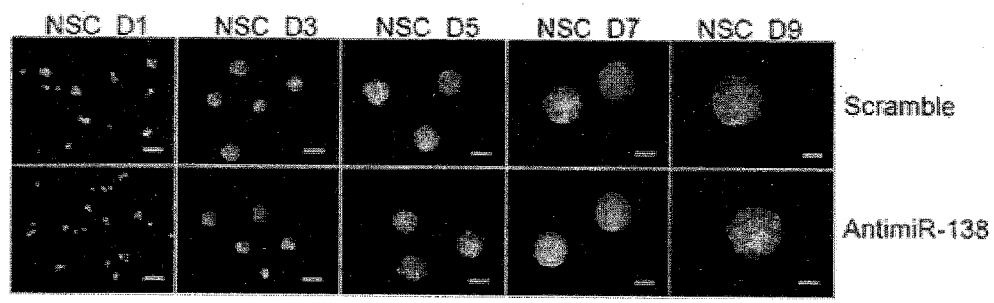
Figure 3:
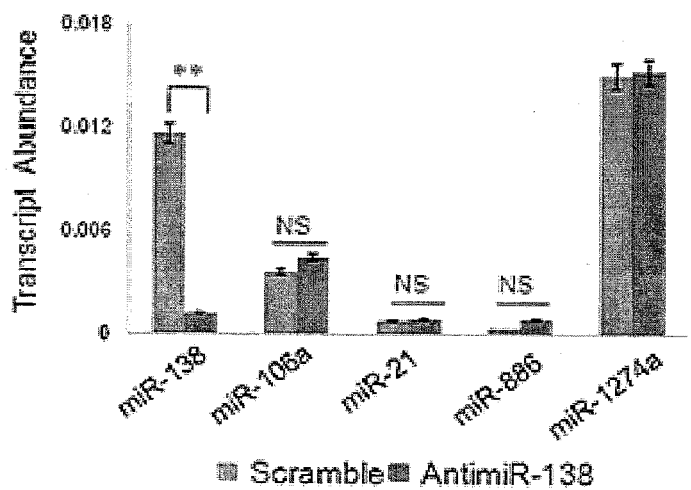

Functional Characterization of Differentially Expressed miRNAs in GSCs—Targeting miR-138 Decreased Neurosphere Formation Capacity of GSCs To understand the functional significance of the elevated expression of miR-138 in GSCs, lentiviral-based antagomirs were used to obtain stable loss-of-function phenotypes (Krutzfeldt et al., 2005 and Scherr et al., 2007). To control for potential off-target effects, a non-targeting-scrambled control (a scramble control) was used. Sequence-specific inhibition of miRNA-138 by a lentiviral vectors encoding an anti-miRNA-138-antagomirs (antimiR-138) affected growth and survival of GSCs (FIG. 3A lower panel) and this is apparent by a decrease in size of tumorspheres compared to the scramble-control (FIGS. 3A and 3B). Results obtained from transduction efficiency assays by FACS and qPCR quantitation of LTRGAG and GFP (vector derived sequences) confirmed that the above-noted antimiR-138 effect was not due to differences in lentivirus transduction or integration efficiency.

Cell-titer growth curve assay demonstrated that the total number of viable scramble-control GSCs increased roughly eight to nine folds over seven days, whereas GSCs depleted of miR-138 decreased in number indicating that miR-138 preferentially contributes to sustained growth of tumor initiating GSCs. FIG. 3C. Clonogenic assays on GSCs transduced with antimiR-138 or scramble-control confirmed the same, wherein 26±1.5% (n=3 independent culture preparations) of wells formed tumorspheres in scramble-control, whereas targeting miR-138 in GSCs prevented tumorspheres formation. FIG. 3D. When single cell suspension of GSCs transduced with antimiR-138 or the scramble-control was plated in soft agar, macroscopically, visible colonies were observed only in GSCs transduced with the scramble-control but not with antimiR-138. FIG. 3E. Together, these results suggest that miR-138 is essential for the growth and survival of bona fide stem cells with self-renewal potential.

To demonstrate the cell-specificity and to rule out toxic effects of antimiR-138 on normal cells, transduced normal human NSCs were transduced with either antimiR-138 or the scramble-control. NSCs were not affected as assessed by their neurosphere formation capacity. FIG. 3F. Further, a significant decrease in the level of only miR-138, and no change in the levels of miR-886, miR-106, miR-21 and miR-1274a in GSCs transduced with antimiR-138 relative to the scramble-control, confirms that antimiR-138 is highly transcript-specific. FIG. 3G.

miR-138 Plays a Pro-Survival Role in GSCs

Figure 4:
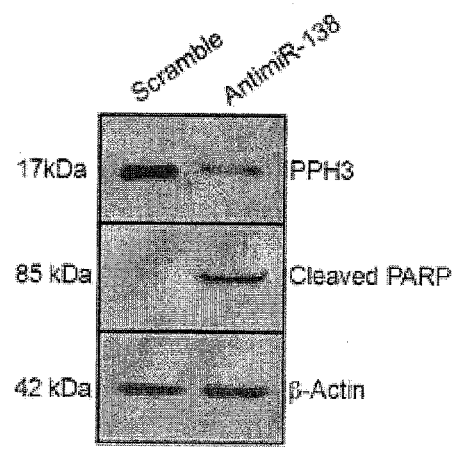
FIG. 4 is a diagram showing that miR-138 is a pro-survival oncomiR. A: a photo showing immunoblot analysis for phosphoprotein histone 3 and cleaved PARP. B: a bar graph showing caspase 3/7 activity relative to cell number increased in antimiR-138-introduced GSCs but not in cells transduced with the scramble control. Data were obtained from a cell titer assay. C: a bar graph showing the percentage of Annexin V positive cells in GSCs transduced with antimiR-138 but not the scramble control. * indicates p<0.01 with t-test comparison of the scramble control and antimiR-138.
Figure 4:
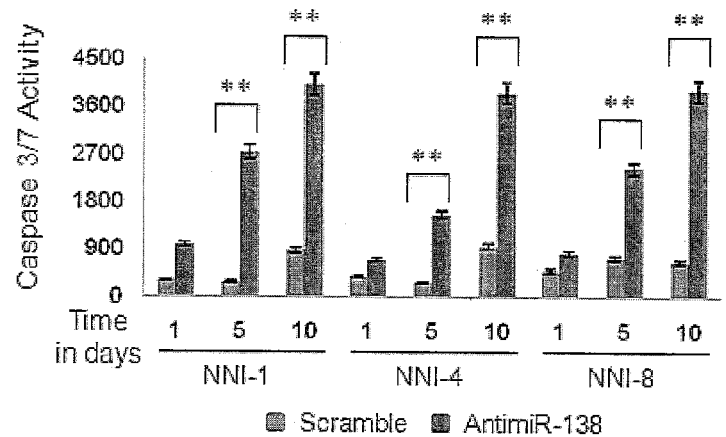
Figure 4:
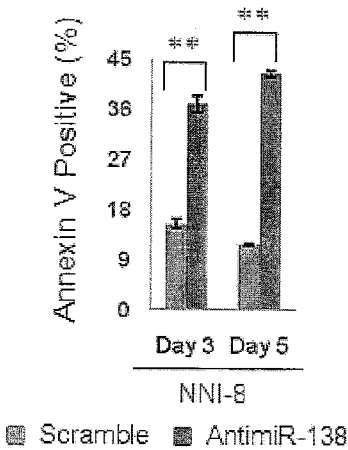

Next, to determine the specific role of miR-138 in regulating proliferation and growth, a dual color flow cytometric analysis with DNA content determination was performed on GSCs transduced with scramble-control or antimiR-138. A reduction in cellular entry into S phase, coupled with reduced expression of phosphohistone H3, a proliferation marker of cells in late $G_2$ and M phase, in GSCs transduced with antimiR-138 but not in cells transduced with the scramble control indicates attenuation of proliferation. A robust increase in subG1 population, accompanied by detection of 89-kDa Poly-ADP-Ribose-Polymerase (PARP) cleavage fraction in GSCs transduced with antimiR-138, but not with the scramble control, suggests that knock-down of miR-138 leads to apoptosis. FIG. 4A. Functional inhibition of miR-138 prevents tumorsphere formation partly due to attenuation of proliferation, coupled with apoptotic cell death of GSCs.

Supporting this result, caspase-3/7 activity normalized to cell number increased in miR-138 targeted GSCs compared to the scramble-control. FIG. 4B. Further targeting miR-138 in GSCs increased the percentage of Annexin V-positive cells when compared to the scramble-control suggesting increased apoptosis. FIG. 4C. Finally, increased terminal deoxynucleotidyl transferase dUTP nick end labeling (TUNEL) staining (detects DNA fragments in the last phase of apoptosis) only in antimiR-138 targeted GSCs, not with the scramble-control, suggests that targeting miR-138 results in increased apoptotic death of GSCs, highlighting that miR-138 is a pro-survival oncomiR for GSCs.

Taken together, the data discussed above demonstrate that targeting miR-138 results in increased apoptotic death of GSCs, indicating that miR-138 is a potential pro-survival oncomiR for GSCs.

miR-138 Promotes Tumorigenesis and is an Essential Pro-Survival oncomiR for GSCs:

To evaluate whether disruption of miR-138 function ablates tumor formation in immunocompromised mice, equal number of viable cells infected with antimiR-138 or the scramble-control were transplanted sub-cutaneously or intracranially in 14 immune-compromised mice. Ten of twelve mice transplanted with GSCs transduced with the scramble developed tumors whereas none of the twelve mice transplanted with GSCs transduced with antimiR-138 GSCs develop tumors. The xenograft tumor sections display GFP and GFAP positive cells confirming that the GFP positive GSCs are tumorigenic. In-situ-hybridization (ISH) on these xeno-graft tumor sections, not normal tissue sections exhibit positive staining for miR-138. This observation coupled with absence of tumor formation in mice bearing antimiR-138 GSCs, suggests that functional knockdown of this pro-survival oncomiR leads to apoptotic death of GSCs and impedes tumor formation.

Figure 5:
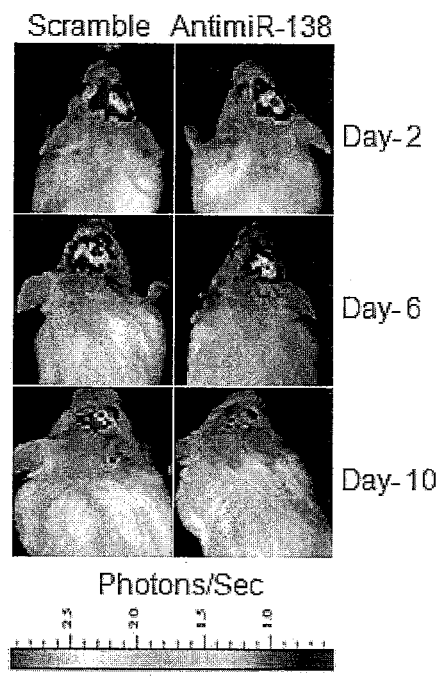
FIG. 5 is a diagram showing that miR-138 is an essential pro-survival oncomiR for GSCs. A: a photo showing the levels of bioluminescence in mice transplanted with luciferase-expressing GSCs transduced with either antimiR-138 or the scramble control. B: a photo of representative micrographic images showing H&E staining of xenograft derived from GSCs transduced with antimiR-138 or the scramble control. H&E staining revealed a large tumor mass only in mice bearing GSCs transduced with the scramble control and no detectable tumor mass was observed in mice implanted with GSCs transduced with antimiR-138. C: a survival plot showing development of intracranial tumors and neurological symptoms only in mice transplanted with GSCs expressing the scramble control but not in mice transplanted with GSCs expressing antimiR-138.
Figure 5:
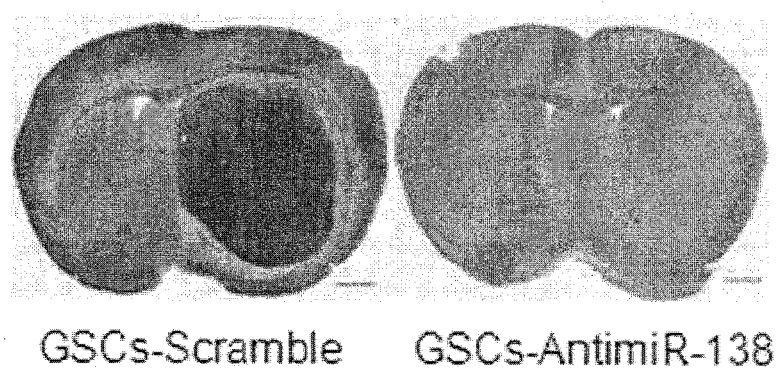
Figure 5:
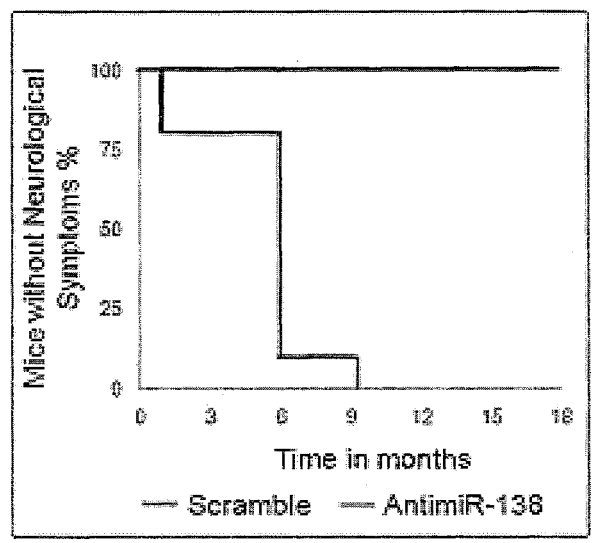
Figure 6:
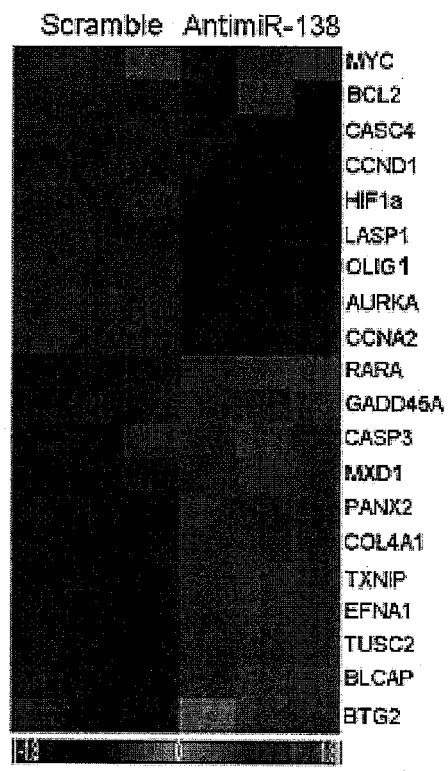
FIG. 6 is a diagram showing that miR-138 targets pro-apoptotic genes and tumor suppressors. A: a graph illustrating expression levels of selected genes as a heat map from microarray data. B: a scatter plot representing the fold changes (Scramble/AntimiR-138) of selected genes obtained from microarray and qRT-PCR. A trend line was plotted by linear regression using the least squares method and $R^2=0.96$. C: a photo showing immuno-blot analysis of CDKN1A, BTG2, OLIG1, EFNA1, LASP1, AURKA, PANX2, TXNIP and GADD45α in GSCs transduced with antimiR-138 or the scramble control. Beta-actin expression was analyzed as the loading control. D: a bar graph showing validation of miR-138 direct targets by Luciferase reporter assays. Luciferase levels are expressed as mean relative to controls±SD.
Figure 6:
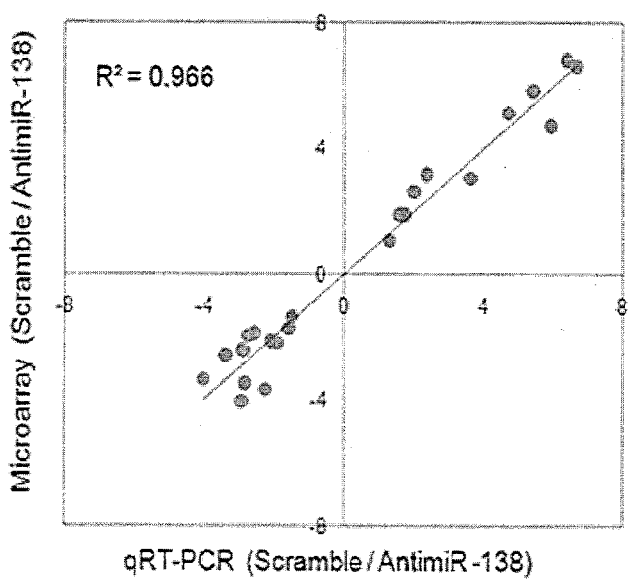
Figure 6:
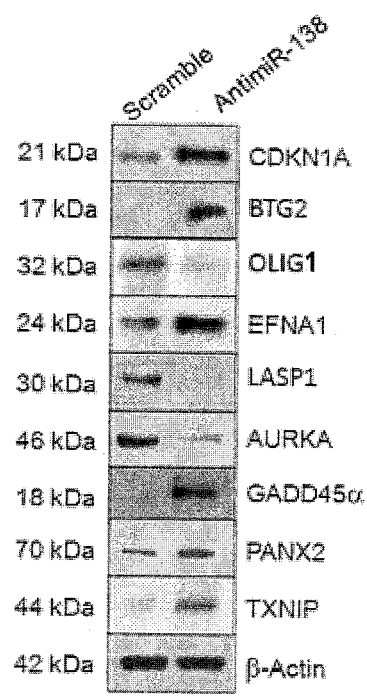
Figure 6:
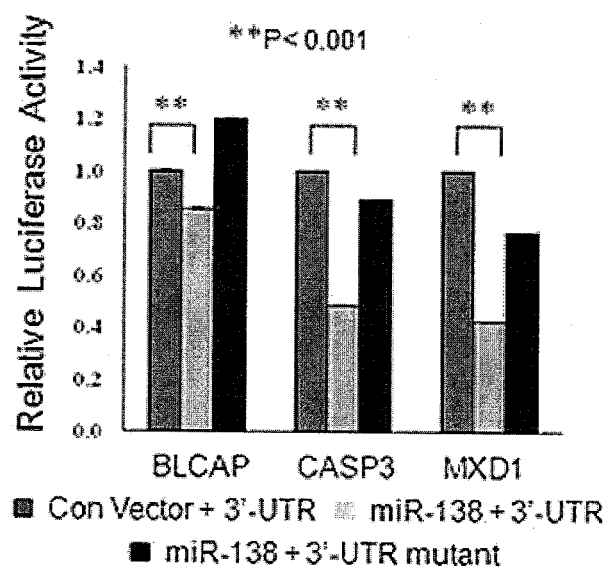

Next, to specifically evaluate the role of miR-138 expression in GSCs and tumorigenicity, luciferase-expressing GSCs transfected with antimiR-138 were intracranially implanted into the forebrains of immune-compromised mice. An equal number of luciferase-expressing GSCs transfected with the non-targeting-scramble RNA was used as a control. The viability of the engrafted GSCs was measured by tracking the bioluminescence after implantation via real-time imaging at various time points as indicated in FIG. 5A. The bioluminescence measured on day-2 after implantation indicates that the antimiR138-transfected GSCs had the same post-transplantation survive rate as the GSCs transfected with the scramble control. However, diminishing luminescence was observed in mice transplanted With the antimiR138-expressing GSCs at day-10, suggesting that miR-138 activity in GSCs relates primarily to the maintenance and survival of GSCs. FIG. 5A. Tumor formation was observed in mice transplanted with GSCs transfected with the scramble control, but not in mice transfected with the antimiR-138-expressing GSCs. FIG. 5B. Further, Mice transplanted with the antimiR-138-expressing GSCs did not show neurological symptoms 18 months after the transplantation, while the percentage of neurological symptom-free mice transplanted with GSCs transfected with the scramble control decreased over time. FIG. 5C. A Kaplan-Meier survival curve also demonstrated increased survival rates in mice transplanted with GSCs transduced with antimiR-138; mice transplanted with GSCs transduced with the scramble control developed tumors and showed a high percentage of mortality. All these results demonstrate that miR-138 positive GSCs are tumorigenic and functional knockdown of this pro-survival oncomiR leads to apoptotic death of GSCs and impedes tumor formation.

miR-138 Targets Tumor Suppressor Genes, Pro-Apoptotic Gene, and Proliferation Inhibitor Genes Further, to delineate the underlying mechanism of miR-138 as a pro-survival oncomiR, targets of miR-138 were identified by comparing gene expression profiles from GSCs transduced with either antimiR-138 or the scramble control. Graphic representation of selected array data as a heatmap, displays several differentially expressed genes. FIG. 6A. For example, MYC, BCL2, CASC4, CCND1, HIF1a, LASP1, OLIG1, AURKA, and CCNA2 were found to be down-regulated in GSCs expressing antigomiR-138 as compared with GSCs expressing the scramble control; and RARA, GADD45A, CASP3, MXD1, PANX2, COL4A1, TXNIP, EFNA1, TUSC2, BLCAP, and BTG2 were found to be up-regulated in GSCs expressing antigomiR-138 as compared with GSCs expressing the scramble control. An excellent linear correlation between array and qRT-PCR ($R^2$=0.96) indicated that the array profiles can be used to ascertain global and specific properties of miR-138. FIG. 6B. Several of the candidate gene products were analyzed by immunoblotting, and expected changes in protein levels were observed. FIG. 6C.

Increased expression of specific genes on functional inhibition of miR-138 suggests that these genes are potential targets of miR-138. These include transcriptional repressors like MAX dimerization protein 1 (MXD1), tumor suppressors like Tumor suppressor candidate 2 (TUSC2) and Bladder cancer-associated protein (BLCAP), pro-apoptotic genes like Cysteine-aspartic acid protease-3 (CASP3) and B-cell translocation gene 2 (BTG2), inhibitors of tumorigenesis like Ephrin-A1 (EFNA1) and Pannexin2 (Panx2), inhibitors of proliferation like retinoic acid receptor, alpha (RARA) and growth arrest and DNA-damage-inducible, alpha (GADD45α), metastasis suppressors like thioredoxin interacting protein (TXNIP), inhibitors of tumor angiogenesis like collagen type IV alpha 1 (COL4A1). FIGS. 6A and 6C.

Interrogation of Targetscan v5.1 database and correlation of the predicted targets with microarray data revealed potential direct targets of miR-138. These include CASP3, BLCAP and MXD1, each with one conserved binding site for miR-138. Chimeric 3'-UTR luciferase reporter assays were performed to confirm the ability of miR-138 to negatively regulate CASP3, MXD1 and BLCAP expression, Expression of miR-138 resulted in significant down-regulation of CASP3, MXD1, or BLCAP 3'-UTR luciferase reporter activity, whereas the reporter vector with a mutation in the miR-138 binding site was not affected confirming that CASP3, MXD1 and BLCAP are direct targets of miR-138. FIG. 6D.

The above-discussed results indicate that miR-138 indirectly activates a plethora of genes involved in tumorigenesis via targeting tumor suppressors, inhibitors of proliferation, and transcriptional repressors, miR-138. Down-regulation of cyclin D1 (CCND1), cyclin A2 (CCNA2), aurora kinase A (AURKA), and proto-oncogene c-Myc (cMYC) by miR-138 inhibition confirms this conclusion. FIGS. 6A and 6C. Concomitant repression of the indirect targets using gene-specific-shRNAs results in a decrease in s-phase population coupled with an increase in sub-G1 population, suggesting that targeting these genes partially phenocopy the effect of antimiR-138 in GSCs. In conclusion, by targeting specific genes, miR-138 promotes proliferation and inhibits apoptosis, underscoring its role as a pro-survival oncomiR.

Figure 7:
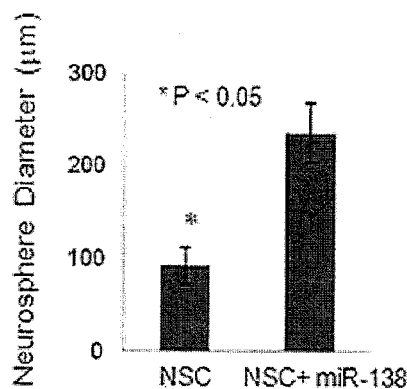
FIG. 7 is a diagram showing the effect of miR-138 over-expression in NSCs. A: a diagram showing the average diameter of neurospheres (n=30) formed by NSCs transduced with an empty vector or miR-138. Lower panel displays neurospheres formed from NSCs transduced with either the scramble control or miR-138. Upper panel is the quantitation of the same (n=30). B: a bar graph showing quantitation of gene expression by quantitative real time PCR analysis in NSCs transduced with miR-138 compared to scramble control.
Figure 7:
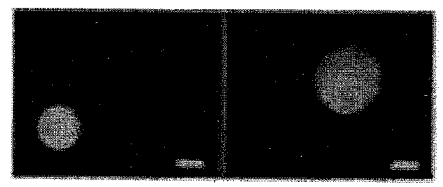
Figure 7:
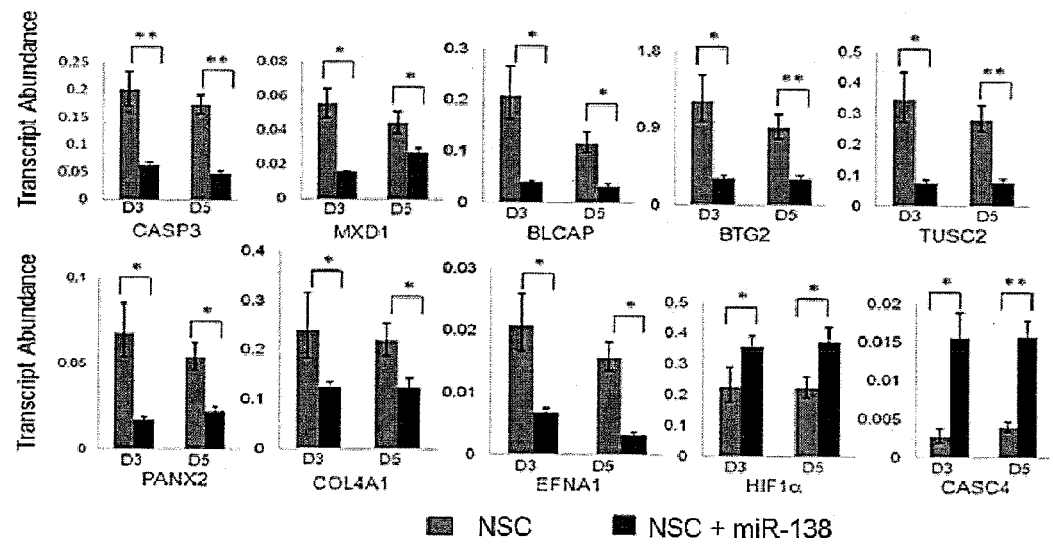
Figure 8:
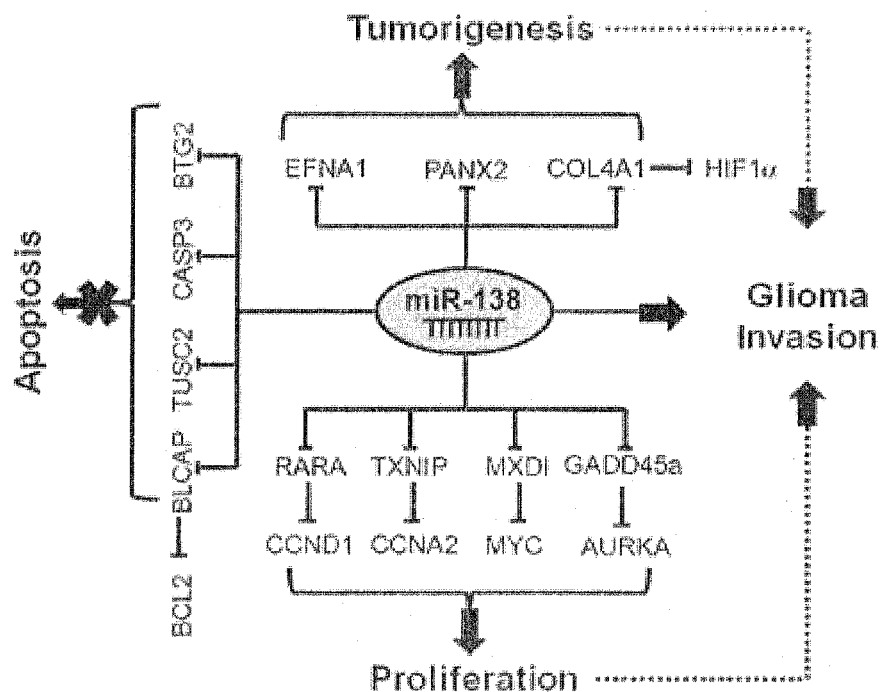
FIG. 8 is a diagram showing miR-138 in GSCs and GBMs. A: a schematic representation of potential targets of miR-138. B: a photo showing patient-derived GBM tumor sections stained by a miR-138 probe via in situ hybridization. C: a log-log plot of the normalized expression levels of miR-138 vs. miR-21 in GBM patient samples. Data was obtained from GEO database (Accession #GSE13030).
Figure 8:
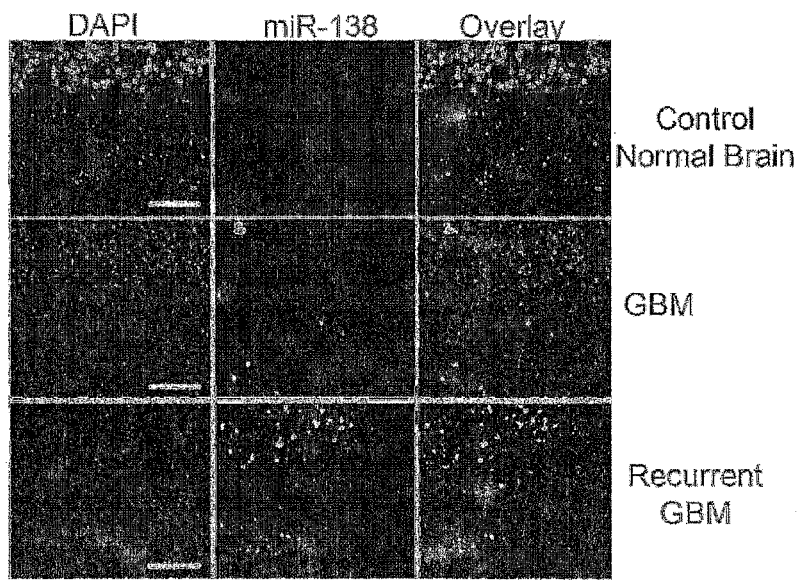
Figure 8:
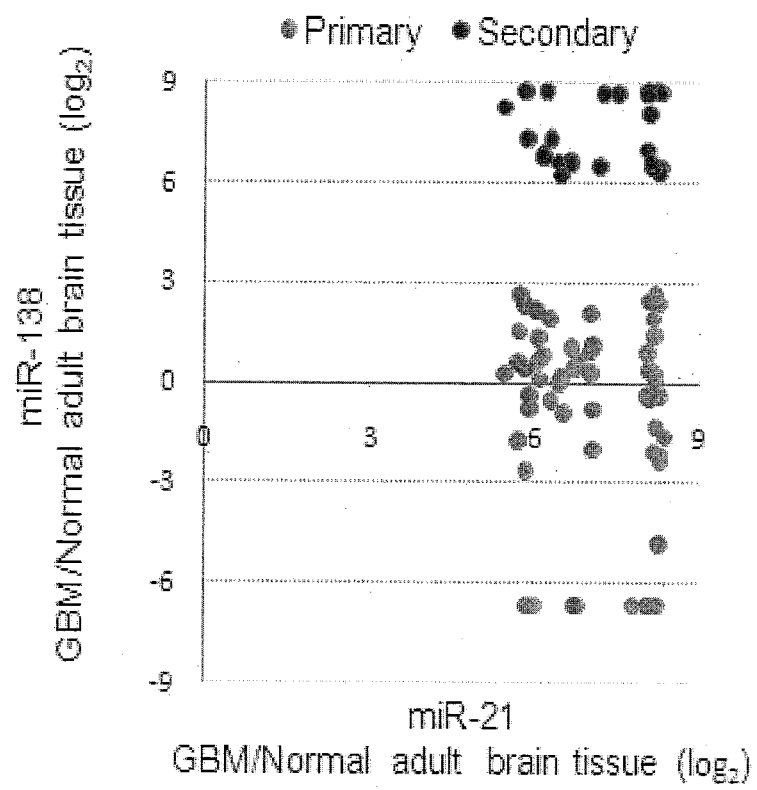

Finally, to test whether the oncomiR-138 alone can confer a transformed phenotype, normal NSCs were transduced with lentivirus expressing miR-138. Ectopic expression of miR-138 in NSCs resulted in a significant increase in size of neurospheres formed when compared with NSCs transduced with the scrambled control. FIG. 7A. Time-course gene expression analysis by qRT-PCR further confirmed that overexpression of miR-138 in NSCs results in a significant down-regulation of several targets accompanied by an increased expression of a few but not all indirect targets. FIG. 7B. These results highlight that miRNA expression is highly context-specific and miR-138 alone may not transform a normal NSC to a GSC.

miR-138—a Potential Prognostic Biomarker:

As a confirmation of clinical significance, and to confirm what we observed above is not a culture artifact, we screened for miR-138 on patient samples. Expression levels of miR-138 in patient tumor specimens were examined by in situ hybridization, using a miR-138-specific probe on patient-derived GBM tumor sections and normal human brain frontal lobe sections. Positive signals were detected inpatient-derived tumor sections stained with the miR-138 specific-probe but not in normal human brain sections stained with the same probe. This result confirms the expression of miR-138 in GBM specimens. FIG. 8B. ISH was performed on 25 patient samples and the results suggested a discrete expression pattern for miR-138 in GBMs. An elevated level of miR-138 was observed in patients with recurrent/secondary GBM, as compared to patients with de novo GBM. FIG. 8B. As a confirmation of clinical significance, GBM patient miRNA profiles were screened in the GEO database (ncbi.nim.nih.gov/geo/query/acc.cgi?acc=GSE13030). In this database from 84 GBM patient samples, 57 patients with primary GBMs display moderate to low expression of miR-138. Supporting the ISH results, 27 patients with secondary/recurrent GBMs displayed a ~150-300 fold increased expression of miR-138 relative to the non-neoplastic adult brain tissue (FIG. 8C), suggesting that miR-138 can serve as a potential prognostic biomarker.

REFERENCES

Amati et al., (1993). Oncogenic activity of the c-Myc protein requires dimerization with Max. Cell 72, 233-245.

Ambros, V. (2004). The functions of animal microRNAs. Nature 431, 350-355. Ayer, D. E., Kretzner, L., and Eisenman, R. N. (1993). Mad: a heterodimeric partner for. Max that antagonizes Myc transcriptional activity. Cell 72, 211-222.

Bagga et al., (2006). Identification and analysis of microRNAs. Genet Eng (N Y) 27, 1-20.

Ball, et al., (1997). Cell-cycle arrest and inhibition of Cdk4 activity by small peptides based on the carboxy-terminal domain of p21WAF1. Curr Biol 7, 71-80.

Bao et al., (2006a). Glioma stem cells promote radioresistance by preferential activation of the DNA damage response. Nature 444, 756-760.

Bao et al., (2006b). Stem cell-like glioma cells promote tumor angiogenesis through vascular endothelial growth factor. Cancer Res 66, 7843-7848.

Bartel, D. P. (2004). MicroRNAs: genomics, biogenesis, mechanism, and function. Cell 116, 281-297.

Bottoni et al., (2005). miR-15a and miR-16-1 down-regulation in pituitary adenomas. J Cell Physiol 204, 280-285.

Calin et al., (2006). MicroRNA signatures in human cancers. Nat Rev Cancer 6, 857-866.

Chang et al., (2008). Widespread microRNA repression by Myc contributes to tumorigenesis. Nat Genet 40, 43-50.

Chong et al., (2009). Cryopreservation of neurospheres derived from human glioblastoma multiforme. Stem Cells 27, 29-39.

Colorado et al., (2000). Anti-angiogenic cues from vascular basement membrane collagen. Cancer Res 60, 2520-2526.

De Santa et al., (2007). The histone H3 lysine-27 demethylase Jmjd3 links inflammation to inhibition of polycomb-mediated gene silencing. Cell 130, 1083-1094.

Esquela-Kerscher et al., (2006). Oncomirs—microRNAs with a role in cancer. Nat Rev Cancer 6, 259-269.

Foong et al., (2011). Cryopreservation of cancer-initiating cells derived from glioblastoma. Front Biosci (Schol Ed) 3, 698-708.

Gal et al., (2008). MIR-451 and Imatinib mesylate inhibit tumor growth of Glioblastoma stem cells. Biochem Biophys Res Commun 376, 86-90.

Galli et al., (2004). Isolation and characterization of tumorigenic, stem-like neural precursors from human glioblastoma. Cancer Res 64, 7011-7021.

Garden et al., (1991). Outcome and patterns of failure following limited-volume irradiation for malignant astrocytomas. Radiother Oncol 20, 99-110.

Geraerts et al., (2006). Comparison of lentiviral vector titration methods. BMC Biotechnol 6, 34.

Goldberg et al., (2003). Melanoma metastasis suppression by chromosome 6: evidence for a pathway regulated by CRSP3 and TXNIP. Cancer Res 63, 432-440.

Griffiths-Jones (2004). The microRNA Registry. Nucleic Acids Res 32, D109-111.

Guessous et al. (2010), microRNA-34a is tumor suppressive in brain tumors and glioma stem cells. Cell Cycle 9.

Han et al., (2003). VDUP1 upregulated by TGF-beta1 and 1,25-dihydroxyvitamin D3 inhibits tumor cell growth by blocking cell-cycle progression. Oncogene 22, 4035-4046.

Hemmati et al., (2003). Cancerous stem cells can arise from pediatric brain tumors. Proc Natl Acad Sci USA 100, 15178-15183.

Ichi et al., (2010) Folic acid remodels chromatin on Hes1 and Neurog2 promoters during caudal neural tube development. J Biol Chem 285, 36922-36932.

Kleihues et al., (1999). Primary and secondary glioblastomas: from concept to clinical diagnosis. Neuro Oncol 1, 44-51.

Kondo et al., (2001). Overexpression of candidate tumor suppressor gene FUS1 isolated from the 3p21.3 homozygous deletion region leads to G1 arrest and growth inhibition of lung cancer cells. Oncogene 20, 6258-6262.

Krutzfeldt et al., (2005). Silencing of microRNAs in vivo with 'antagomirs'. Nature 438, 685-689.

Lagos-Quintana et al., (2002). Identification of tissue-specific microRNAs from mouse. Curr Biol 12, 735-739.

Lai et al., (2009). Pannexin2 as a novel growth regulator in C6 glioma cells. Oncogene 28, 4402-4408.

Legler et al., (1999). Cancer surveillance series [corrected]: brain and other central nervous system cancers: recent trends in incidence and mortality. J Natl Cancer Inst 91, 1382-1390.

Li et al., (2009a). MicroRNA-34a inhibits glioblastoma growth by targeting multiple oncogenes. Cancer Res 69, 7569-7576.

Li et al., (2009b). Hypoxia-inducible factors regulate tumorigenic capacity of glioma stem cells. Cancer Cell 15, 501-513.

Lisanti et al., (2010). Understanding the "lethal" drivers of tumor-stroma co-evolution: emerging role(s) for hypoxia, oxidative stress and autophagy/mitophagy in the tumor micro-environment. Cancer Biol Ther 10, 537-542.

Liu et al., (2007). Ephrin-A1 is a negative regulator in glioma through down-regulation of EphA2 and FAK. Int J Oncol 30, 865-871.

Lu et al., (2005). MicroRNA expression profiles classify human cancers. Nature 435, 834-838.

Ma et al., (2007). Tumour invasion and metastasis initiated by microRNA-10b in breast cancer. Nature 449, 682-688.

Nyberg et al., (2008). Characterization of the anti-angiogenic properties of arresten, an alpha1beta1 integrin-dependent collagen-derived tumor suppressor. Exp Cell Res 314, 3292-3305.

Obad et al., (2011). Silencing of microRNA families by seed-targeting tiny LNAs. Nat Genet 43, 371-378.

Obernosterer et al., (2006). Post-transcriptional regulation of microRNA expression. RNA 12, 1161-1167.

Papagiannakopoulos et al., (2008). MicroRNA-21 targets a network of key tumor-suppressive pathways in glioblastoma cells. Cancer Res 68, 8164-8172.

Reya et al., (2001). Stein cells, cancer, and cancer stem cells. Nature 414, 105-111.

Reynolds et al., (2005). Neural stem cells and neurospheres—re-evaluating the relationship. Nat Methods 2, 333-336.

Rouault et al., (1996). Identification of BTG2, an antiproliferative p53-dependent component of the DNA damage cellular response pathway. Nat Genet 14, 482-486.

Scherr et al., (2007). Lentivirus-mediated antagomir expression for specific inhibition of miRNA function. Nucleic Acids Res 35, e149.

Shao et al., (2006). Gadd45a interacts with aurora-A and inhibits its kinase activity. J Biol Chem 281, 28943-28950.

Shin et al., (2008). VDUP1 mediates nuclear export of HIF1alpha via CRM1-dependent pathway. Biochim Biophys Acta 1783, 838-848.

Silber et al., (2008). miR-124 and miR-137 inhibit proliferation of glioblastoma multiforme cells and induce differentiation of brain tumor stem cells. BMC Med 6, 14.

Singh et al., (2004). Identification of human brain tumour initiating cells. Nature 432, 396-401.

Slack et al., (2006). MicroRNAs as a potential magic bullet in cancer. Future Oncol 2, 73-82.

Sudhakar et al., (2005). Human alpha1 type IV collagen NC1 domain exhibits distinct antiangiogenic activity mediated by alpha1beta1 integrin. J Clin Invest 115, 2801-2810.

Tiscornia et al., (2006). Production and purification of lentiviral vectors. Nat Protoc 1, 241-245.

Traenka et al., (2010). Role of LIM and SH3 protein 1 (LASP1) in the metastatic dissemination of medulloblastoma. Cancer Res 70, 8003-8014.

Wang et al., (2009). Loss of CAK phosphorylation of RAR{alpha} mediates transcriptional control of retinoid-induced cancer cell differentiation. Faseb J 24, 833-843.

Wang et al., (2008). c-Myc is required for maintenance of glioma cancer stem cells. PLoS One 3, e3769.

Weber (2005). New human and mouse microRNA genes found by homology search. FEBS J 272, 59-73.

Yao et al., (2007). Overexpression of BLCAP induces S phase arrest and apoptosis independent of p53 and NF-kappaB in human tongue carcinoma: BLCAP overexpression induces S phase arrest and apoptosis. Mol Cell Biochem 297, 81-92.

Zhao et al., (2010) miR-138 might reverse multidrug resistance of leukemia cells. Leuk Res 34, 1078-1082.

Zheng et al., (2008). Pten and p53 converge on c-Myc to control differentiation, self-renewal, and transformation of normal and neoplastic stem cells in glioblastoma. Cold Spring Harb Symp Quant Biol 73, 427-437.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A pharmaceutical composition, comprising an oligonucleotide targeting miR-138, wherein the oligonucleotide comprises the nucleotide sequence of 5'-GAGCTGGTAT-TGTGAATCAAGCAGCTTCCTGTCAGCG-GCCTGATTCACA ACACCAGCTTTTTT3' (SEQ ID NO:2).

2. The pharmaceutical composition of claim 1, wherein the amount of the oligonucleotide is effective in suppressing glioma stem cell proliferation or inducing apoptosis in glioma stem cells.

3. The pharmaceutical composition of claim 1, wherein one or more of the nucleotides in the oligonucleotide are modified by a 2'-O-methoxy group, a 2'-O-methoxyethyl group, or a phosphorothioate group.

* * * * *

SEQUENCE LISTING

```
<160> NUMBER OF SEQ ID NOS: 64

<210> SEQ ID NO 1
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 1
cggcctgatt cacaacacca gct                                               23

<210> SEQ ID NO 2
<211> LENGTH: 63
<212> TYPE: DNA
<213> ORGANISM: Homo sapiens

<400> SEQUENCE: 2
gagctggtat tgtgaatcaa gcagcttcct gtcagcggcc tgattcacaa caccagcttt      60
ttt                                                                    63

<210> SEQ ID NO 3
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 3
```

```
cttcctgtca g                                                  11

<210> SEQ ID NO 4
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 4
caggcaacgt ggcgtggtg                                          19

<210> SEQ ID NO 5
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 5
ggcgatgagt tccgccgtg                                          19

<210> SEQ ID NO 6
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 6
tgtgtgcccg tctgttgtgt gac                                     23

<210> SEQ ID NO 7
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 7
tcgggcgcca ctgctagag                                          19

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 8
agagcaccaa aggcgccctg                                         20

<210> SEQ ID NO 9
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 9
tgcgggtgtt ggtgtagc                                           18

<210> SEQ ID NO 10
<211> LENGTH: 18
<212> TYPE: DNA
<213> ORGANISM: Artificial Sequence
```

```
<220> FEATURE:
<223> OTHER INFORMATION: Synthetic Oligonucleotide

<400> SEQUENCE: 10
gcctcctggc ttgcctgg                                                 18

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 11
tggtgggcct ggagtccctg                                               20

<210> SEQ ID NO 12
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 12
cagagcacta caaacaccac tg                                            22

<210> SEQ ID NO 13
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 13
ctgagtccga tctggctg                                                 18

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
gcggctgggg caggttatgg                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
ccgagctttg gacccgctgg                                               20

<210> SEQ ID NO 16
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 16
gtcggtggcg agctgagg                                                 18
```

```
<210> SEQ ID NO 17
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 17
caccaaggca gcagggatc                                                 19

<210> SEQ ID NO 18
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 18
ccccagtcca aggaccaag                                                 19

<210> SEQ ID NO 19
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 19
ctgtgagtga ttttgccact g                                              21

<210> SEQ ID NO 20
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 20
cctggatgct ggaggtctg                                                 19

<210> SEQ ID NO 21
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 21
acatgcaagt ggcccccag                                                 19

<210> SEQ ID NO 22
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 22
gggctgtcaa ggccgtagc                                                 19

<210> SEQ ID NO 23
<211> LENGTH: 18
<212> TYPE: DNA
<213> ORGANISM: Artificial Sequence
<220> FEATURE:
<223> OTHER INFORMATION: Synthetic Oligonucleotide
```

-continued

```
<400> SEQUENCE: 23
ccacggcact cagacagg                                                   18

<210> SEQ ID NO 24
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 24
tgatcccgcc gtccactc                                                   18

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 25
gtgcaacccg tctcgtcttc                                                 20

<210> SEQ ID NO 26
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 26
ccaactggac aacctctctc c                                               21

<210> SEQ ID NO 27
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 27
gctgcggatc aacaggggat tc                                              22

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 28
cggagtggcg gagcgtcaag                                                 20

<210> SEQ ID NO 29
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 29
tgggcaatgg agtgagacc                                                  19

<210> SEQ ID NO 30
```

<210> SEQ ID NO 30
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 30
tcaccacatc ccgaccag                                                   18

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 31
cggcgctgta gtcatacacc                                                 20

<210> SEQ ID NO 32
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 32
cagatcgcgt ccgcgggatt c                                               21

<210> SEQ ID NO 33
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 33
tggtcgccaa gtccaaag                                                   18

<210> SEQ ID NO 34
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 34
agggcgttcc tgaagggcgt c                                               21

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
gcgcctggga aaccgcatag                                                 20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
gtggacctcg gattagcctc                                            20

<210> SEQ ID NO 37
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 37
gctcatcgct ggaactgatt g                                          21

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
atttggctac agcaacaggg                                            20

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
tgtgaggagg ggagattcag                                            20

<210> SEQ ID NO 40
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 40
ggggaggatt gtggccttc                                             19

<210> SEQ ID NO 41
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 41
cagggcgatg ttgtccacc                                             19

<210> SEQ ID NO 42
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 42
ggtaacagtt gtcgatctcc tg                                         22

<210> SEQ ID NO 43
<211> LENGTH: 21
<212> TYPE: DNA

<213> ORGANISM: Artificial Sequence
<220> FEATURE:
<223> OTHER INFORMATION: Synthetic Oligonucleotide

<400> SEQUENCE: 43
ccaagaactt cgcagaggaa c                                              21

<210> SEQ ID NO 44
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 44 agagggatc gttgtagaag tc                                              22

<210> SEQ ID NO 45
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 45
acagtccagt tctgtaccac g                                              21

<210> SEQ ID NO 46
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 46
agtgcaaaca gacttcggag                                                20

<210> SEQ ID NO 47
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 47
tttgtctctt gagttggctg g                                              21

<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
agccgttcac caaatcgacc                                                20

<210> SEQ ID NO 49
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 49
ctcgtcagag tcgctcac                                                  18

<210> SEQ ID NO 50
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 50
ccctgatcca ggcgttttg                                              19

<210> SEQ ID NO 51
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 51
gatccatgta gcgactttcc                                             20

<210> SEQ ID NO 52
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 52
cctccactcg gaaggactat c                                           21

<210> SEQ ID NO 53
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 53
aagctccgtt ttagctcgtt c                                           21

<210> SEQ ID NO 54
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 54
cagcagccag acgatcatgc a                                           21

<210> SEQ ID NO 55
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 55
tggtcagctg tggtaatcca ctttca                                      26

<210> SEQ ID NO 56
<211> LENGTH: 17
<212> TYPE: DNA
<213> ORGANISM: Artificial Sequence
<220> FEATURE:

<223> OTHER INFORMATION: Synthetic Oligonucleotide

<400> SEQUENCE: 56
ctcgcttcgg cagcaca                                                          17

<210> SEQ ID NO 57
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 57
aacgcttcac gaatttgcgt                                                       20

<210> SEQ ID NO 58
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 58
ccctggcatg gtgtggtg                                                         18

<210> SEQ ID NO 59
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 59
agtgtggtgt ggccctggtg                                                       20

<210> SEQ ID NO 60
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 60
gttgctgcag ctggtgttgt g                                                     21

<210> SEQ ID NO 61
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 61
gccgggtaag aggatgcgct g                                                     21

<210> SEQ ID NO 62
<211> LENGTH: 99
<212> TYPE: DNA
<213> ORGANISM: Homo sapiens

<400> SEQUENCE: 62
ccctggcatg gtgtggtggg gcagctggtg ttgtgaatca ggccgttgcc aatcagagaa           60
cggctacttc acaacaccag ggccacacca cactacagg                                  99

```
<210> SEQ ID NO 63
<211> LENGTH: 84
<212> TYPE: DNA
<213> ORGANISM: Homo sapiens

<400> SEQUENCE: 63
cgttgctgca gctggtgttg tgaatcaggc cgacgagcag cgcatcctct tacccggcta        60
tttcacgaca ccagggttgc atca                                               84

<210> SEQ ID NO 64
<211> LENGTH: 23
<212> TYPE: DNA
<213> ORGANISM: Homo sapiens

<400> SEQUENCE: 64
agctggtgtt gtgaatcagg ccg                                                23
```